United States Patent
Wariar et al.

(10) Patent No.: US 8,000,780 B2
(45) Date of Patent: Aug. 16, 2011

(54) DETECTION OF MYOCARDIAL ISCHEMIA FROM THE TIME SEQUENCE OF IMPLANTED SENSOR MEASUREMENTS

(75) Inventors: Ramesh Wariar, Blaine, MN (US); Veerichetty Kadhiresan, Centerville, MN (US); Richard Fogoros, Pittsburg, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1232 days.

(21) Appl. No.: 11/426,835

(22) Filed: Jun. 27, 2006

(65) Prior Publication Data
US 2007/0299356 A1    Dec. 27, 2007

(51) Int. Cl.
*A61B 5/04* (2006.01)
(52) U.S. Cl. ............... 600/513; 600/508; 607/5; 607/9
(58) Field of Classification Search ............... 600/508, 600/509, 513; 607/5, 9
See application file for complete search history.

(56) References Cited

U.S. PATENT DOCUMENTS

| | | | |
|---|---|---|---|
| 3,703,900 A | 11/1972 | Holznagel | |
| 3,716,059 A | 2/1973 | Welborn et al. | |
| 3,799,147 A | 3/1974 | Adolph et al. | |
| 3,910,260 A | 10/1975 | Sarnoff et al. | |
| 4,004,577 A | 1/1977 | Sarnoff | |
| 4,094,308 A | 6/1978 | Cormier | |
| 4,289,141 A | 9/1981 | Cormier | |
| 4,428,378 A | 1/1984 | Anderson et al. | |
| 4,432,374 A | 2/1984 | Osanai | |
| 4,446,872 A | 5/1984 | Marsoner et al. | |
| 4,548,204 A | 10/1985 | Groch et al. | |
| 4,562,846 A | 1/1986 | Cox et al. | |
| 4,585,004 A | 4/1986 | Brownlee | |
| 4,586,514 A | 5/1986 | Schlager et al. | |
| 4,649,930 A | 3/1987 | Groch et al. | |
| 4,674,518 A | 6/1987 | Salo | |
| 4,679,144 A | 7/1987 | Cox et al. | |
| 4,686,987 A | 8/1987 | Salo et al. | |
| 4,702,253 A | 10/1987 | Nappholz et al. | |
| 4,763,646 A | 8/1988 | Lekholm | |

(Continued)

FOREIGN PATENT DOCUMENTS

EP    0308536 A1    3/1989

(Continued)

OTHER PUBLICATIONS

"U.S. Appl. No. 10/334,694, Final Office Action mailed Oct. 7, 2008", 14 pgs.

(Continued)

*Primary Examiner* — Carl H Layno
*Assistant Examiner* — Pamela M Bays
(74) *Attorney, Agent, or Firm* — Schwegman, Lundberg & Woessner, P.A.

(57) ABSTRACT

A system including a plurality of implantable sensors, a processor, and a response circuit. Each sensor produces an electrical sensor signal related to physiologic cardiovascular events of a subject. The processor includes an event sequence detector to permit real-time detection of a time-wise sequential cascade of physiologic cardiovascular events related to myocardial ischemia of a subject and a decision module. The time-wise cascade includes at least first, second, and third physiologic cardiovascular events. The decision module declares whether an ischemic event occurred using at least one rule applied to a temporal relationship of the first, second, and third physiologic cardiovascular events. The response circuit provides a specified response if the ischemic event is declared.

30 Claims, 7 Drawing Sheets

U.S. PATENT DOCUMENTS

| | | | |
|---|---|---|---|
| 4,773,401 A | 9/1988 | Citak et al. |
| 4,796,639 A | 1/1989 | Snow et al. |
| 4,798,211 A | 1/1989 | Goor et al. |
| 4,821,735 A | 4/1989 | Goor et al. |
| 4,905,706 A | 3/1990 | Duff et al. |
| 4,915,113 A | 4/1990 | Holman |
| 4,924,875 A | 5/1990 | Chamoun |
| 4,945,909 A | 8/1990 | Fearnot et al. |
| 4,967,760 A | 11/1990 | Bennett et al. |
| 4,981,139 A | 1/1991 | Pfohl |
| 4,989,611 A | 2/1991 | Zanetti et al. |
| 5,007,427 A | 4/1991 | Suzuki et al. |
| 5,010,889 A | 4/1991 | Bredesen et al. |
| 5,012,815 A | 5/1991 | Bennett, Jr. et al. |
| 5,020,540 A | 6/1991 | Chamoun |
| 5,025,809 A | 6/1991 | Johnson et al. |
| 5,054,496 A | 10/1991 | Wen et al. |
| 5,072,458 A | 12/1991 | Suzuki |
| 5,111,818 A | 5/1992 | Suzuki et al. |
| 5,137,019 A | 8/1992 | Pederson et al. |
| 5,159,932 A | 11/1992 | Zanetti et al. |
| 5,179,947 A | 1/1993 | Meyerson et al. |
| 5,190,035 A | 3/1993 | Salo et al. |
| 5,199,428 A | 4/1993 | Obel et al. |
| 5,218,969 A | 6/1993 | Bredesen et al. |
| 5,228,449 A | 7/1993 | Christ et al. |
| 5,265,602 A | 11/1993 | Anderson et al. |
| 5,284,136 A | 2/1994 | Hauck et al. |
| 5,301,679 A | 4/1994 | Taylor |
| 5,324,310 A | 6/1994 | Greeninger et al. |
| 5,331,966 A | 7/1994 | Bennett et al. |
| 5,334,222 A | 8/1994 | Salo et al. |
| 5,337,752 A | 8/1994 | Reeves |
| 5,365,932 A | 11/1994 | Greenhut |
| 5,366,487 A | 11/1994 | Adams et al. |
| 5,391,190 A | 2/1995 | Pederson et al. |
| 5,417,717 A | 5/1995 | Salo et al. |
| 5,472,453 A | 12/1995 | Alt |
| 5,485,849 A | 1/1996 | Panescu et al. |
| 5,487,752 A | 1/1996 | Salo et al. |
| 5,496,361 A | 3/1996 | Moberg et al. |
| 5,505,202 A | 4/1996 | Mogi et al. |
| 5,520,191 A | 5/1996 | Karlsson et al. |
| 5,531,767 A | 7/1996 | Fain |
| 5,544,661 A | 8/1996 | Davis et al. |
| 5,554,177 A | 9/1996 | Kieval et al. |
| 5,584,868 A | 12/1996 | Salo et al. |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,725,562 A | 3/1998 | Sheldon |
| 5,776,168 A | 7/1998 | Gunderson |
| 5,792,066 A | 8/1998 | Kwong |
| 5,792,195 A | 8/1998 | Carlson et al. |
| 5,819,741 A | 10/1998 | Karlsson et al. |
| 5,824,021 A | 10/1998 | Rise |
| 5,833,621 A | 11/1998 | Panescu et al. |
| 5,836,987 A | 11/1998 | Baumann et al. |
| 5,860,933 A | 1/1999 | Don Michael |
| 5,891,045 A | 4/1999 | Albrecht et al. |
| 5,935,081 A | 8/1999 | Kadhiresan |
| 5,991,661 A | 11/1999 | Park et al. |
| 6,002,777 A | 12/1999 | Grasfield et al. |
| 6,009,349 A | 12/1999 | Mouchawar et al. |
| 6,016,443 A | 1/2000 | Ekwall et al. |
| 6,021,350 A | 2/2000 | Mathson |
| 6,022,322 A | 2/2000 | Prutchi |
| 6,026,324 A | 2/2000 | Carlson |
| 6,038,469 A | 3/2000 | Karlsson et al. |
| 6,044,297 A | 3/2000 | Sheldon et al. |
| 6,044,298 A | 3/2000 | Salo et al. |
| 6,044,299 A | 3/2000 | Nilsson |
| 6,045,513 A | 4/2000 | Stone et al. |
| 6,047,206 A | 4/2000 | Albrecht |
| 6,053,872 A | 4/2000 | Mohler |
| 6,058,329 A | 5/2000 | Salo et al. |
| 6,064,910 A | 5/2000 | Andersson et al. |
| 6,076,015 A | 6/2000 | Hartley et al. |
| 6,077,227 A | 6/2000 | Miesel |
| 6,108,577 A | 8/2000 | Benser |
| 6,112,116 A | 8/2000 | Fischell et al. |
| 6,128,526 A | 10/2000 | Stadler et al. |
| 6,144,880 A | 11/2000 | Ding et al. |
| 6,152,884 A | 11/2000 | Bjorgaas |
| 6,161,042 A | 12/2000 | Hartley et al. |
| 6,171,256 B1 | 1/2001 | Joo et al. |
| 6,179,865 B1 | 1/2001 | Hsu et al. |
| 6,193,668 B1 | 2/2001 | Chassaing et al. |
| 6,208,900 B1 | 3/2001 | Ecker et al. |
| 6,217,525 B1 | 4/2001 | Medema et al. |
| 6,223,082 B1 | 4/2001 | Bakels et al. |
| 6,230,059 B1 | 5/2001 | Duffin |
| 6,233,486 B1 | 5/2001 | Ekwall et al. |
| 6,264,606 B1 | 7/2001 | Ekwall et al. |
| 6,264,611 B1 | 7/2001 | Ishikawa et al. |
| 6,272,377 B1 | 8/2001 | Sweeney et al. |
| 6,272,379 B1 | 8/2001 | Fischell et al. |
| 6,273,856 B1 | 8/2001 | Sun et al. |
| 6,278,894 B1 | 8/2001 | Salo et al. |
| 6,285,898 B1 | 9/2001 | Ben-Haim |
| 6,298,269 B1 | 10/2001 | Sweeney |
| 6,312,378 B1 | 11/2001 | Bardy |
| 6,314,323 B1 | 11/2001 | Ekwall et al. |
| 6,319,205 B1 | 11/2001 | Goor et al. |
| 6,334,071 B1 | 12/2001 | Lu |
| 6,351,672 B1 | 2/2002 | Park et al. |
| 6,351,673 B1 | 2/2002 | Ding et al. |
| 6,360,127 B1 | 3/2002 | Ding et al. |
| 6,361,522 B1 | 3/2002 | Scheiner et al. |
| 6,366,811 B1 | 4/2002 | Carlson |
| 6,368,283 B1 | 4/2002 | Xu et al. |
| 6,368,284 B1 | 4/2002 | Bardy |
| 6,370,424 B1 | 4/2002 | Prutchi |
| 6,381,493 B1 | 4/2002 | Stadler et al. |
| 6,405,083 B1 | 6/2002 | Rockwell et al. |
| 6,409,675 B1 | 6/2002 | Turcott |
| 6,411,840 B1 | 6/2002 | Bardy |
| 6,415,033 B1 | 7/2002 | Halleck et al. |
| 6,440,082 B1 | 8/2002 | Joo et al. |
| 6,456,871 B1 | 9/2002 | Hsu et al. |
| 6,459,929 B1 | 10/2002 | Hopper et al. |
| 6,466,821 B1 | 10/2002 | Pianca et al. |
| 6,468,263 B1 | 10/2002 | Fischell et al. |
| 6,477,406 B1 | 11/2002 | Turcott |
| 6,478,746 B2 | 11/2002 | Chassaing et al. |
| 6,480,733 B1 | 11/2002 | Turcott |
| 6,491,639 B1 | 12/2002 | Turcott |
| 6,493,579 B1 | 12/2002 | Gilkerson et al. |
| 6,496,715 B1 | 12/2002 | Lee et al. |
| 6,505,067 B1 | 1/2003 | Lee et al. |
| 6,512,940 B1 | 1/2003 | Brabec et al. |
| 6,514,195 B1 | 2/2003 | Ferek |
| 6,520,924 B2 | 2/2003 | Lee |
| 6,522,917 B1 | 2/2003 | Hsu et al. |
| 6,522,925 B1 | 2/2003 | Gilkerson et al. |
| 6,526,313 B2 | 2/2003 | Sweeney et al. |
| 6,527,729 B1 | 3/2003 | Turcott |
| 6,531,907 B2 | 3/2003 | Dooley et al. |
| 6,542,775 B2 | 4/2003 | Ding et al. |
| 6,575,916 B2 | 6/2003 | Halleck et al. |
| 6,604,000 B2 | 8/2003 | Lu |
| 6,609,023 B1 | 8/2003 | Fischell et al. |
| 6,625,493 B2 | 9/2003 | Kroll et al. |
| 6,626,842 B2 | 9/2003 | Oka |
| 6,643,548 B1 | 11/2003 | Mai et al. |
| 6,650,940 B1 | 11/2003 | Zhu et al. |
| 6,658,283 B1 | 12/2003 | Bornzin et al. |
| 6,665,564 B2 | 12/2003 | Lincoln et al. |
| 6,666,826 B2 | 12/2003 | Salo et al. |
| 6,684,103 B2 | 1/2004 | Ding et al. |
| 6,687,540 B2 | 2/2004 | Marcovecchio |
| 6,721,591 B2 | 4/2004 | Wei |
| 6,733,464 B2 | 5/2004 | Olbrich et al. |
| 6,768,919 B2 | 7/2004 | Starobin et al. |
| 6,792,308 B2 | 9/2004 | Corbucci |

| Patent/Publication | Date | Name |
|---|---|---|
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,827,690 B2 | 12/2004 | Bardy |
| 6,830,548 B2 | 12/2004 | Bonnet et al. |
| 6,845,263 B2 | 1/2005 | Kawaguchi |
| 6,885,889 B2 | 4/2005 | Chinchoy |
| 6,937,899 B2 * | 8/2005 | Sheldon et al. ............... 607/18 |
| 6,942,622 B1 * | 9/2005 | Turcott ......................... 600/508 |
| 6,985,771 B2 | 1/2006 | Fischell et al. |
| 7,039,462 B2 | 5/2006 | Pastore et al. |
| 7,043,305 B2 | 5/2006 | KenKnight et al. |
| 7,066,891 B2 | 6/2006 | Stadler et al. |
| 7,072,711 B2 | 7/2006 | Girouard et al. |
| 7,115,096 B2 | 10/2006 | Siejko et al. |
| 7,139,609 B1 | 11/2006 | Min et al. |
| 7,171,258 B2 | 1/2007 | Goode |
| 7,181,268 B2 | 2/2007 | Sheldon et al. |
| 7,181,269 B1 | 2/2007 | Kroll |
| 7,190,996 B2 | 3/2007 | Jarverud |
| 7,203,535 B1 | 4/2007 | Hsu et al. |
| 7,212,849 B2 | 5/2007 | Zhang et al. |
| 7,215,992 B2 | 5/2007 | Stahmann et al. |
| 7,215,997 B2 | 5/2007 | Yu et al. |
| 7,228,176 B2 | 6/2007 | Smith et al. |
| 7,248,923 B2 | 7/2007 | Maile et al. |
| 7,299,086 B2 | 11/2007 | McCabe et al. |
| 7,299,087 B2 | 11/2007 | Bardy |
| 7,364,547 B2 | 4/2008 | Stahmann et al. |
| 7,369,892 B2 | 5/2008 | Ferek-Petric |
| 7,415,307 B2 | 8/2008 | Sharma et al. |
| 7,479,112 B2 | 1/2009 | Sweeney et al. |
| 7,512,439 B1 | 3/2009 | Farazi |
| 7,539,533 B2 | 5/2009 | Tran |
| 7,558,623 B2 | 7/2009 | Fischell et al. |
| 7,567,836 B2 | 7/2009 | Zhang |
| 7,577,478 B1 | 8/2009 | Kroll et al. |
| 7,751,890 B2 | 7/2010 | McCabe et al. |
| 7,844,334 B2 | 11/2010 | Maile et al. |
| 2002/0001390 A1 | 1/2002 | Kawaguchi |
| 2002/0035337 A1 | 3/2002 | Oka |
| 2002/0049474 A1 | 4/2002 | Marcovecchio et al. |
| 2002/0065539 A1 | 5/2002 | Von Arx et al. |
| 2002/0072684 A1 | 6/2002 | Stearns |
| 2002/0072778 A1 | 6/2002 | Guck et al. |
| 2002/0082645 A1 | 6/2002 | Sweeney |
| 2002/0107450 A1 | 8/2002 | Ogura |
| 2002/0107552 A1 | 8/2002 | Krig et al. |
| 2002/0111551 A1 | 8/2002 | Van Erlach et al. |
| 2002/0120205 A1 | 8/2002 | Ferek-Petric |
| 2002/0123768 A1 | 9/2002 | Gilkerson |
| 2002/0123769 A1 | 9/2002 | Panken et al. |
| 2002/0128563 A1 | 9/2002 | Carlson et al. |
| 2002/0143372 A1 | 10/2002 | Snell et al. |
| 2002/0147401 A1 | 10/2002 | Oka |
| 2002/0151811 A1 | 10/2002 | Starobin et al. |
| 2002/0151812 A1 | 10/2002 | Scheiner et al. |
| 2002/0151938 A1 | 10/2002 | Corbucci |
| 2002/0198461 A1 | 12/2002 | Hsu et al. |
| 2003/0004549 A1 | 1/2003 | Hill et al. |
| 2003/0004552 A1 | 1/2003 | Plombon et al. |
| 2003/0013974 A1 | 1/2003 | Natarajan et al. |
| 2003/0023175 A1 | 1/2003 | Arzbaecher et al. |
| 2003/0040676 A1 | 2/2003 | Prentice et al. |
| 2003/0045908 A1 | 3/2003 | Condie et al. |
| 2003/0055352 A1 | 3/2003 | Hayek et al. |
| 2003/0055461 A1 | 3/2003 | Girouard et al. |
| 2003/0060849 A1 | 3/2003 | Hsu |
| 2003/0069608 A1 | 4/2003 | Sweeney |
| 2003/0069609 A1 | 4/2003 | Thompson |
| 2003/0072458 A1 | 4/2003 | Halleck et al. |
| 2003/0078624 A1 | 4/2003 | Carlson et al. |
| 2003/0083586 A1 | 5/2003 | Ferek-Petric |
| 2003/0093002 A1 | 5/2003 | Kuo |
| 2003/0093003 A1 | 5/2003 | Watrous et al. |
| 2003/0105491 A1 | 6/2003 | Gilkerson et al. |
| 2003/0109792 A1 | 6/2003 | Hsu et al. |
| 2003/0114889 A1 | 6/2003 | Huvelle et al. |
| 2003/0120159 A1 | 6/2003 | Mohler |
| 2003/0120316 A1 | 6/2003 | Spinelli et al. |
| 2003/0125774 A1 | 7/2003 | Salo |
| 2003/0139778 A1 | 7/2003 | Fischell et al. |
| 2003/0144702 A1 | 7/2003 | Yu et al. |
| 2003/0144703 A1 | 7/2003 | Yu et al. |
| 2003/0158492 A1 | 8/2003 | Sheldon et al. |
| 2003/0171791 A1 | 9/2003 | KenKnight et al. |
| 2003/0176798 A1 | 9/2003 | Simon |
| 2003/0176896 A1 | 9/2003 | Lincoln et al. |
| 2003/0191402 A1 | 10/2003 | Arzbaecher et al. |
| 2003/0191503 A1 | 10/2003 | Zhu et al. |
| 2003/0216620 A1 | 11/2003 | Jain et al. |
| 2003/0229289 A1 | 12/2003 | Mohler |
| 2003/0233130 A1 | 12/2003 | Padmanabhan et al. |
| 2004/0015081 A1 | 1/2004 | Kramer et al. |
| 2004/0015090 A1 | 1/2004 | Sweeney et al. |
| 2004/0024423 A1 | 2/2004 | Lincoln et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0059238 A1 | 3/2004 | Fischell et al. |
| 2004/0064056 A1 | 4/2004 | Ogura |
| 2004/0073093 A1 | 4/2004 | Hatlestad |
| 2004/0078059 A1 | 4/2004 | Ding et al. |
| 2004/0078060 A1 | 4/2004 | Ding et al. |
| 2004/0088017 A1 | 5/2004 | Sharma et al. |
| 2004/0093035 A1 | 5/2004 | Schwartz et al. |
| 2004/0102712 A1 | 5/2004 | Belalcazar et al. |
| 2004/0106960 A1 | 6/2004 | Siejko et al. |
| 2004/0106961 A1 | 6/2004 | Siejko et al. |
| 2004/0111040 A1 | 6/2004 | Ni et al. |
| 2004/0116820 A1 | 6/2004 | Daum et al. |
| 2004/0116972 A1 | 6/2004 | Marcovecchio |
| 2004/0122478 A1 | 6/2004 | Stadler et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0004476 A1 | 1/2005 | Payvar et al. |
| 2005/0004485 A1 * | 1/2005 | Crosby et al. ............... 600/513 |
| 2005/0010257 A1 | 1/2005 | Lincoln et al. |
| 2005/0027323 A1 | 2/2005 | Mulligan et al. |
| 2005/0033190 A1 | 2/2005 | Bauer |
| 2005/0038345 A1 | 2/2005 | Gorgenberg et al. |
| 2005/0043639 A1 | 2/2005 | Fischell |
| 2005/0043675 A1 | 2/2005 | Pastore et al. |
| 2005/0060001 A1 | 3/2005 | Singhal et al. |
| 2005/0065445 A1 | 3/2005 | Arzbaecher et al. |
| 2005/0065448 A1 | 3/2005 | Stahmann et al. |
| 2005/0065556 A1 * | 3/2005 | Reghabi et al. .................. 607/5 |
| 2005/0102001 A1 | 5/2005 | Maile et al. |
| 2005/0137631 A1 | 6/2005 | Yu et al. |
| 2005/0148896 A1 | 7/2005 | Siejko et al. |
| 2005/0148897 A1 | 7/2005 | Cho et al. |
| 2005/0149136 A1 | 7/2005 | Siejko et al. |
| 2005/0159666 A1 | 7/2005 | Pearce et al. |
| 2005/0159781 A1 | 7/2005 | Hsu et al. |
| 2005/0197674 A1 | 9/2005 | McCabe et al. |
| 2005/0256417 A1 | 11/2005 | Fischell et al. |
| 2005/0256542 A1 | 11/2005 | Pastore et al. |
| 2005/0283195 A1 | 12/2005 | Pastore et al. |
| 2005/0288721 A1 | 12/2005 | Girouard et al. |
| 2006/0009811 A1 | 1/2006 | Sheldon et al. |
| 2006/0015148 A1 | 1/2006 | McCabe et al. |
| 2006/0020294 A1 | 1/2006 | Brockway et al. |
| 2006/0020295 A1 | 1/2006 | Brockway et al. |
| 2006/0025699 A1 | 2/2006 | Maile et al. |
| 2006/0030892 A1 | 2/2006 | Kadhiresan et al. |
| 2006/0052717 A1 | 3/2006 | Mugler et al. |
| 2006/0116593 A1 | 6/2006 | Zhang et al. |
| 2006/0247686 A1 | 11/2006 | Girouard et al. |
| 2006/0247700 A1 | 11/2006 | Jackson |
| 2006/0253044 A1 | 11/2006 | Zhang |

| | | | |
|---|---|---|---|
| 2006/0259087 A1 | 11/2006 | Baynham et al. |
| 2006/0282000 A1 | 12/2006 | Zhang et al. |
| 2006/0287684 A1 | 12/2006 | Baynham et al. |
| 2007/0038256 A1 | 2/2007 | Maschke |
| 2007/0043393 A1 | 2/2007 | Brockway et al. |
| 2007/0049835 A1 | 3/2007 | Goode |
| 2007/0054871 A1 | 3/2007 | Pastore et al. |
| 2007/0078491 A1 | 4/2007 | Siejko et al. |
| 2007/0093720 A1 | 4/2007 | Fischell et al. |
| 2007/0129639 A1 | 6/2007 | Zhang |
| 2007/0150005 A1 | 6/2007 | Sih et al. |
| 2007/0150015 A1 | 6/2007 | Zhang et al. |
| 2007/0162081 A1 | 7/2007 | Yu et al. |
| 2007/0179392 A1 | 8/2007 | Zhang |
| 2007/0203524 A1 | 8/2007 | Sheldon et al. |
| 2007/0208263 A1 | 9/2007 | John et al. |
| 2007/0249944 A1 | 10/2007 | Fischell et al. |
| 2007/0276453 A1 | 11/2007 | Hill et al. |
| 2007/0293775 A1 | 12/2007 | Fischell et al. |
| 2008/0015652 A1 | 1/2008 | Maile et al. |
| 2008/0051672 A1 | 2/2008 | McCabe et al. |
| 2008/0058660 A1 | 3/2008 | Fischell et al. |
| 2008/0058661 A1 | 3/2008 | Bardy |
| 2008/0081354 A1 | 4/2008 | Qu et al. |
| 2008/0082135 A1 | 4/2008 | Arcot et al. |
| 2008/0091138 A1 | 4/2008 | Pastore et al. |
| 2008/0139954 A1 | 6/2008 | Day et al. |
| 2008/0177156 A1 | 7/2008 | Zhang et al. |
| 2008/0177194 A1 | 7/2008 | Zhang et al. |
| 2008/0183091 A1 | 7/2008 | Fischell et al. |
| 2008/0188762 A1 | 8/2008 | John et al. |
| 2008/0188763 A1 | 8/2008 | John et al. |
| 2008/0228094 A1 | 9/2008 | Audet et al. |
| 2009/0025459 A1 | 1/2009 | Zhang et al. |
| 2009/0048528 A1 | 2/2009 | Hopenfeld et al. |
| 2009/0082682 A1 | 3/2009 | Fischell et al. |
| 2009/0082781 A1 | 3/2009 | Tran et al. |
| 2009/0124916 A1 | 5/2009 | Sweeney et al. |
| 2009/0171228 A1 | 7/2009 | Fischell et al. |
| 2009/0177103 A1 | 7/2009 | Bharmi |
| 2009/0287106 A1 | 11/2009 | Zhang et al. |
| 2011/0022109 A1 | 1/2011 | McCabe et al. |

FOREIGN PATENT DOCUMENTS

| | | |
|---|---|---|
| EP | 0744190 A2 | 11/1996 |
| EP | 0784996 A1 | 7/1997 |
| WO | WO-94/01173 A1 | 1/1994 |
| WO | WO-97/25098 A1 | 7/1997 |
| WO | WO-00/07497 A1 | 2/2000 |
| WO | WO-01/08748 A1 | 2/2001 |
| WO | WO-01/30436 A2 | 5/2001 |
| WO | WO-01/56651 A1 | 8/2001 |
| WO | WO-03/041797 A2 | 5/2003 |
| WO | WO-2004/012815 A1 | 2/2004 |
| WO | WO-2004/050178 A1 | 6/2004 |
| WO | WO-2004//060483 A1 | 7/2004 |
| WO | WO-2005/089643 A1 | 9/2005 |
| WO | WO-2005/122902 A1 | 12/2005 |
| WO | WO-2006028575 A2 | 3/2006 |

OTHER PUBLICATIONS

"U.S. Appl. No. 10/334,694, Response filed Dec. 3, 2007 to Final Office Action mailed Oct. 1, 2007", 21 pgs.

"U.S. Appl. No. 10/334,694, Response filed Dec. 8, 2008 to Final Office Action mailed Oct. 7, 2008", 18 pgs.

"U.S. Appl. No. 10/334,694, Response filed Jun. 19, 2008 to Non-Final Office Action mailed Mar. 19, 2008", 20 pgs.

"U.S. Appl. No. 10/334,694, Advisory Action mailed Dec. 23, 2008", 3 pgs.

"U.S. Appl. No. 10/334,694, Non-Final Office Action Apr. 20, 2007", 12 pgs.

"U.S. Appl. No. 10/334,694, Non-Final Office Action Nov. 27, 2006", 9 pgs.

"U.S. Appl. No. 10/334,694, Non-Final Office Action mailed Mar. 19, 2008", 15 pgs.

"U.S. Appl. No. 10/334,694, Response filed Feb. 27, 2007 to Non-Final Office Action Nov. 27, 2006", 20 pgs.

"U.S. Appl. No. 10/334,694, Response filed Jul. 20, 2007 to Non-Final Office Action mailed Apr. 20, 2007", 18 pgs.

"U.S. Appl. No. 10/334,694, Final Office Action mailed Oct. 1, 2007", 13 pgs.

"U.S. Appl. No. 10/334,694, Non-Final Office Action mailed Mar. 18, 2009", 14 pgs.

"U.S. Appl. No. 10/703,175, Final Office Action mailed Oct. 12, 2006", 9 pgs.

"U.S. Appl. No. 10/703,175, Non-Final Office Action mailed May 10, 2006", 7 pgs.

"U.S. Appl. No. 10/703,175, Notice of Allowance mailed Mar. 19, 2007", 5 pgs.

"U.S. Appl. No. 10/703,175, Response filed Dec. 12, 2006 to Final Office Action mailed Oct. 12, 2006", 21 pgs.

"U.S. Appl. No. 10/703,175, Response filed Aug. 9, 2006 to Non-Final Office Action mailed May 10, 2006", 20 pgs.

"U.S. Appl. No. 10/746,874, Notice of Allowance mailed May 19, 2006", 9 pgs.

"U.S. Appl. No. 10/746,874, Response filed Apr. 17, 2006 to Restriction Requirement mailed Mar. 31, 2006", 14 pgs.

"U.S. Appl. No. 10/746,874, Restriction Requirement mailed Mar. 31, 2006", 6 pgs.

"U.S. Appl. No. 10/795,126, Non-Final Office Action mailed Jan. 25, 2007", 12 pgs.

"U.S. Appl. No. 10/795,126, Notice of Allowance mailed Jul. 9, 2007", 10 pgs.

"U.S. Appl. No. 10/795,126, Response filed Apr. 25, 2007 to Non-Final Office Action mailed Jan. 25, 2007", 11 pgs.

"U.S. Appl. No. 10/865,498 Non-Final Office Action mailed Sep. 11, 2006", 7 pgs.

"U.S. Appl. No. 10/865,498 Notice of Allowance mailed Dec. 6, 2006", 7 pgs.

"U.S. Appl. No. 10/865,498 Response filed Oct. 24, 2006 to Non-Final Office Action mailed Sep. 11, 2006", 19 pgs.

"U.S. Appl. No. 11/129,050, Restriction Requirement mailed Aug. 1, 2007", 6 pgs.

"U.S. Appl. No. 11/129,050, Advisory Action mailed Jul. 28, 2008", 3 pgs.

"U.S. Appl. No. 11/129,050, Final Office Action mailed May 12, 2008", 8 pgs.

"U.S. Appl. No. 11/129,050, Non-Final Office Action mailed Nov. 26, 2007", 7 pgs.

"U.S. Appl. No. 11/129,050, Response filed Sep. 28, 2007 to Restriction Requirement mailed Aug. 1, 2007", 11 pgs.

"U.S. Appl. No. 11/129,050, Response filed Feb. 23, 2009 to Non Final Office Action mailed Nov. 6, 2008", 13 pgs.

"U.S. Appl. No. 11/129,050, Response filed Feb. 26, 2008 to Non-Final Office Action mailed Nov. 26, 2007", 14 pgs.

"U.S. Appl. No. 11/129,050, Response filed Jul. 14, 2008 to Final Office Action mailed May 12, 2008", 13 pgs.

"U.S. Appl. No. 11/129,050, Supplemental Amendment and Response filed Sep. 12, 2008 to Final Office Action mailed May 12, 2008 and the Advisory Action mailed Jul. 28, 2008", 12 pgs.

"U.S. Appl. No. 11/129,050, Non-Final Office Action mailed Nov. 6, 2008", 7 pgs.

"U.S. Appl. No. 11/129,050, Final Office Action mailed Apr. 21, 2009", 10 pgs.

"U.S. Appl. No. 11/148,107, Restriction Requirement mailed May 30, 2008", 6 pgs.

"U.S. Appl. No. 11/148,107, Final Office Action mailed Jan. 14, 2009", 10 pgs.

"U.S. Appl. No. 11/148,107, Response filed Oct. 20, 2008 to Non-Final Office Action mailed Jul. 18, 2008", 9 pgs.

"U.S. Appl. No. 11/148,107, Response filed Jun. 30, 2008 to Restriction Requirement mailed May 30, 2008", 7 pgs.

"U.S. Appl. No. 11/148,107, Non-Final Office Action mailed Jul. 18, 2008", 7 pgs.

"U.S. Appl. No. 11/148,107, Notice of Allowance mailed Mar. 30, 2009", 4 pgs.

"U.S. Appl. No. 11/148,107, Response filed Mar. 16, 2009 to Final Office Action mailed Jan. 14, 2009", 9 pgs.

"U.S. Appl. no. 11/113,828, Non-Final Office Action mailed Mar. 5, 2008", 8 pgs.

U.S. Appl. no. 11/113,828, Response filed Jun. 5, 2008 to Non-Final Office Action mailed Mar. 5, 2008, 8 pgs.
"U.S. Appl. No. 11/113,828, Restriction Requirement mailed Dec. 26, 2007", 6 pgs.
"U.S. Appl. No. 11/113,828, Response filed Jan. 28, 2008 to Restriction Requirement mailed Dec. 26, 2007", 7 pgs.
"U.S. Appl. No. 11/113,828, Non Final Office Action mailed Dec. 22, 2008", 10 pgs.
"U.S. Appl. No. 11/113,828, Response filed Mar. 23, 2009 to Non Final Office Action mailed Dec. 22, 2008", 8 pgs.
"U.S. Appl. No. 11/113,828, Final Office Action mailed Sep. 17, 2008", 10 pgs.
"U.S. Appl. No. 11/113,828, Response filed Nov. 17, 2008 to Final Office Action mailed Sep. 17, 2008", 11 pgs.
"International Application Search No. PCT/US2005/006984, International Search Report and Written Opinion mailed Aug. 4, 2005", 13 pgs.
Aaron, S. D, et al., "How accurate is spirometry at predicting restrictive pulmonary impairment?", *Chest*, 115(3), (Mar. 1999), 869-873.
Adolph, R. J., et al., "The clinical value of frequency analysis of the first heart sound in myocardial infarction.", *Circulation*, 41(6), (Jun. 1970), 1003-14.
Amende, I. et al., "Hemodynamics in ischemia: diastolic phase", *Z. Kardiol.*, 73 Suppl 2, [Article in German With English Abstract], (1984), 127-133.
Auricchio, A., et al., "Cardiac Resynchronization Therapy Restores Optimal Atrioventricular Mechanical Timing in Heart Failure Patients with Ventricular Conduction Delay", *Journal of the American College of Cardiology*, 39(7), (2002), 1163-1169.
Auricchio, A., et al., "Dynamically Optimized Multisite Cardiac Resynchronizer", U.S. Appl. No. 10/071,875, filed Feb. 8. 2002, 22 pgs.
Breithardt, O A, et al., "Acute effects of cardiac resynchronization therapy on functional mitral regurgitation in advanced systolic heart failure", *Journal of the American College of Cardiology*, 41(5), (May 21, 2003), 765-70.
Brockway, M., et al., "Method and Appartus for Monitoring Heart Failure Patients With Cardiopulmonary Comorbidities", U.S. Appl. No. 10/897,856, filed Jul. 23, 2004, 54 pgs.
Brockway, Marina, et al., "Method and Apparatus for Optimization of Cardiac Resynchronization Therapy Using Heart Sounds", U.S. Appl. No. 10/865,498, filed Jun. 10, 2004, 45 pgs.
Bulgrin, J. R, et al., "Comparison of Short-Time Fourier, Wavelet and Time-Domain Analyses of Intracardiac Sounds", *Biomedical Sciences Instrumentation*, 29, (1993), 4 pgs.
Carabello, B A, "Mitral valve disease", *Current Problems in Cardiology*,18(7), (Jul. 1993), 425-478.
Carlson, G. M, et al., "Hemodynamic Stability Assessment Based on Heart Sounds", U.S. Appl. No. 11/277,773, filed Mar. 29, 2006, 39 pgs.
Carr, W. N., "Integrated Pressure Sensor With Remote Power Source and Remote Readout", *The 8th International Conference on Solid-State Sensors and Actuators and Eurosensors IX, Digest of Technical Papers*, Stockholm, Sweden, (Jun. 25-29, 1995), 624-627.
Clarke, W. B., et al., "Spectral Energy of the First Heart Sound in Acute Myocardial Ischemia. A Correlation with Electrocardiographic, Hemodynamic, and Wall Motion Abnormalities.", *Circulation*, 57(3), (Mar. 1978), 593-598.
Collins, S., "Diagnostic Utility of an S3 in Dyspneic ED Patients", *Inovise Medical Inc, University of Cincinnati Medical Center*, (2005), 6 pgs.
Ding, J., et al., "Cardiac Pacing Using Adjustable Atrio-Ventricular Delays", U.S. Appl. No. 10/008,830, filed Dec. 7, 2001, 42 pgs.
Ding, J., et al., "Cardiac Pacing Using Adjustable Atrio-Ventricular Delays", U.S. Appl. No. 10/243,811, filed Sep. 13, 2002, 39 pgs.
Dzwonczyk, R., et al., "Myocardial electrical impedance responds to ischemia and reperfusion in humans", *IEEE Transactions on Biomedical Engineering*, 51(12), (Dec. 2004), 2206-2209.
Fenster, M. S., et al., "Mitral regurgitation: an overview", *Curr Probl Cardiol.*, 20(4), (Apr. 1995), 193-280.
Hada, Y., et al., "Pulsus alternans determined by biventricular simultaneous systolic time intervals", *Circulation*, 65(3), (Mar. 1982), 617-26.

Hsu, W., "System and Method for Classifying Tachycardia Arrhyhmias Having 1:1 Atrial to Ventricular Rhythms", U.S. Appl. No. 09/417,588, filed Oct. 13, 1999, 39 pgs.
Hughes, H. C, et al., "The Effects of Electrode Position on the Detection of the Transvenous Cardiac Electrogram", *PACE*, vol. 3, (Nov.-Dec. 1980), 651-655.
Kinderman, M., et al., "Optimizing the AV Delay in DDD Pacemaker Patients with High Degree AV Block: Mitral Valve Doppler Versus Impedance Cardiography", *PACE*, vol. 20, (Oct. 1997), 2453-2462.
Konta, T., et al., "Significance of Discordant ST Alternans in Ventricular Fibrillation", *Circulation*, 82(6), (Dec. 1990), 2185-2189.
Krayenbühl, H. P., "Hemodynamics in ischemia. Systolic phase", *Z. Kardiol.*, 73 Suppl 2, [Article in German with English Abstract], (1984), 119-125.
Leatham, A, "Splitting of the First and Second Heart Sounds", *Lancet*, 267 (6839), (1954), 607-614.
Lee, Y. C, et al., "Pulsus alternans in patients with congestive cardiomyopathy", *Circulation*, 65(7), (Jun. 1982), 1533-1534.
Leitch, J., et al., "Feasibility of an Implantable Arrhythmia Monitor", *PACE*, vol. 15, No. 12, (Dec. 1992), 2232-2235.
Leonelli, F. M, et al., "Systolic and Diastolic Effects of Variable Atroventricular Delay and Patients with Complete Hear Block and Normal Ventricular Function", *Amer. J-Cardiology*, vol. 80, (Aug. 1, 1997), 294-298.
Lincoln, W. C., "Classifying Tachyarrhythmia Using Time Interval Between Ventricular Depolarization and Mitral Valve Closure", U.S. Appl. No. 10/618,261, filed Jul. 11, 2003, 26 pgs.
Maile, K. R., et al., "A Dual-Use Sensor for Rate Responsive Pacing and Heart Sound Monitoring", U.S. Appl. No. 10/703,175, filed Nov. 6, 2003, 41 pgs.
Maile, K. R., et al., "Determining A Patient's Posture From Mechanical Vibrations of the Heart", U.S. Appl. No. 10/900,570, filed Jul. 28, 2004, 24 pgs.
Mazur, A., "Functional similarity between electrograms recorded from an implantable cardioverter defibrillator emulator and the surface electrocardiogram", *PACE*, vol. 24, (Jan. 2001), 34-40.
McCabe, A., "Self-Diagnostic Method and System for Implantable Cardiac Device", U.S. Appl. No. 10/890,810, filed Jul. 14, 2004, 18 pgs.
Min, M., "Electrical Impedance and Cardiac Monitoring-Technology, Potential and Applications", *International Journal of Bioelectromagnetism*, 5(1), (2003), 53-56.
Nesto, R. W., et al., "The ischemic cascade: temporal sequence of hemodynamic, electrocardiographic and symptomatic expressions of ischemia.", *American Journal of Cardiology*, 59(7), (Mar. 9, 1987), 23C-30C.
Obaidat, M. S, et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technological Challenges of the 1990s, (1992), 856-862.
Panju, A, A, et al., "Is This Patient Having a Myocardial Infraction?", *JAMA*, 280(14), (Oct. 14, 1998), 1256-1263.
Pastore, J. M., et al., "Method and Apparatus for Detecting Acoustic Oscillations in Cardiac Rhythm", U.S. Appl. No. 10/138,046, filed May 3, 2002, 25 pgs.
Pastore, Joseph M, "Method and Apparatus for Detecting Oscillations in Cardiac Rhythm", U.S. Appl. No. 10/172,825, filed Jun. 14, 2002, 33 pgs.
Patangay, A., et al., "Ischemia Detection Using Heart Sound Timing", U.S. Appl. No. 11/625,003, filed Jan. 19, 2007, 69 pgs.
Prinzen, F. W, "Mapping of regional myocardial strain and work during ventricular pacing: experimental study using magnetic resonance imaging tagging", *Journal of the American College of Cardiology*, 33(6), (May 1999), 1735-1742.
Ritter, P., et al., "New Method for Determining the Optimal Atrio-Ventricular Delay in Patients Place in DDD Mode for Complete Atrio-Ventricular Block", *NASPE Abstract #237, Pacing and Clinical Electrophysiology*, (1995), p. 885.
Rosa, A., et al., "Ectopic Pacing at Physiological Rate Improves Postanoxic Recovery of the Developing Heart", *Am. J. Physiol.— Heart Circ. Physiol.*, 284, (2003), H2384-H2392.

Sakamoto, T., et al., "Hemodynamic Determinants of the Amplitude of the First Heart Sound", *Circulation Research*, 16, (1965), 45-57.

Salerno, D. M., "Seismocardiography for Monitoring Changes in Left Ventricular Function during Ischemia.", *Chest*, 100(4), (Oct. 1991), 991-993.

Say, O, et al., "Classification of heart sounds by using wavelet transform", *24th Annual Conference and the Annual Fall Meeting of the Biomedical Engineering Society] EMBS/BMES Conference*vol. 1, (2002), 128-129.

Schaefer, Saul, et al., "Clinical and hemodynamic characteristics of patients with inducible pulsus alternans", *American Heart Journal*, vol. 115, No. 6, (Jun. 1988), 1251-1257.

Sheiban, I., et al., "Time course and determinants of left ventricular function recovery after primary angioplasty in patients with acute myocardial infarction", *J Am Coll Cardiol.*, 38(2), (Aug. 2001), 464-471.

Siejko, K. Z., et al., "Method for Correction of Posture Dependence on Heart Sounds", U.S. Appl. No. 11/037,275, filed Jan. 18, 2005, 26 pgs.

Siejko, K, Z., "A Third Heart Sound Activity Index for Heart Failure Monitoring", U.S. Appl. No. 10/746,874, filed Dec. 24 2003, 41 pgs.

Siejko, K. Z., et al., "Method and Apparatus for Third Heart Sound Detection", U.S. Appl. No. 10/746,853, filed Dec. 24 2003, 40 pgs.

Smith, Damon, et al., "Influence of the Aortic Component of the Second Heart Sound on Left Ventricular Maximal Negative dP/dt in the Dog", *Am. J. Cardiol.*, 55: 205, (1985), 205-209.

Smith, V., "Systems, Devices and Methods for Tachyarrythmia Discrimination or Therapy Decisions", U.S. Appl. No. 10/897,365, filed Jul. 22, 2004, 38 pgs.

Stahmann, J., et al., "Thoracic Impedance Detection With Blood Resistivity Compensation", U.S. Appl. No. 10/921,503, filed Aug. 19, 2004, 38 pgs.

Stein, E., et al.,"Rapid Interpretation of Heart Sounds and Murmurs", *Baltimore : Williams & Wilkins, 4th ed.*, (1997), 85-105.

Tavel, M. E, "The Appearance of Gallop Rhythm after Exercise Stress Testing", *Clin. Cardiol.*, vol. 19, (1996), 887-891.

Theres, H. P, et al., "Detection of acute myocardial ischemia during percutaneous transluminal coronary angioplasty by endocardial acceleration.", *Pacing Clin Electrophysiol.*, vol. 27, No. 5, (May 2004), 621-625.

Theres, H., et al., "Electrogram signals recorded from acute and chronic pacemaker implantation sites in pacemaker patie", *PACE*, vol. 21, Part 1, (Jan. 1998), 11-17.

Theroux, P., et al., "Regional Myocardial function in the conscious dog during acute coronary occlusion and responses to morphine, propranolol, nitroglycerin, and lidocaine.", *Circulation*, 53(2), (Feb. 1976), 302-314.

Vegh, A, et al., "Transient ischaemia induced by rapid cardiac pacing results in myocardial preconditioning", *Cardiovascular Research*, 25(12), (Dec. 1991), 1051-1053.

Wariar, R., et al., "Systems and Methods for Multi-Axis Cardiac Vibration Measurements", U.S. Appl. No. 11/135,985, filed May 24, 2004, 35 pgs.

Wariar, R., et al., "Detection of Myocardial Ischemia From the Time Sequence of Implanted Sensor Measurements", U.S. Appl. No. 11/426,835, filed Jun. 27, 2006, 41 pgs.

Wood, J. C, et al., "Time-Frequency Transforms: A New Approach to First Heart Sound Frequency Dynamics", *IEEE Transactions on Biomedical Engineering*, 39 (7), IEEE Service Center, US, (1992), 730-740.

Yu, Yinghong, et al., "Method and Apparatus for Optimizing Stroke Volume During DDD Resynchronization Therapy Using Adjustable Atrio-Ventricular Delays", U.S. Appl. No. 10/314,899, filed Dec. 9, 2002, 50 pgs.

Yu, Yi., et al., "Method and Apparatus for Optimizing Ventricular Synchrony During DDD Resynchronization Therapy Using Adjustable Atrio-Ventricular Delays", U.S. Appl. No. 10/314,910, filed Dec. 9, 2002, 50 pgs.

Zhang, Y., et al., "Ischemia Detection Using a Heart Sound Sensor", U.S. Appl. No. 11/148,107, filed Jun. 8, 2005, 41 pgs.

Zin, Z M, et al., "Wavelet analysis and classification of Mitral regurgitation and normal heart sounds based on artificial neural networks", *Seventh International Symposium on Signal Processing and Its Applications*, vol. 2, (Jul. 1-4, 2003), 619-620.

"U.S. Appl. No. 11/148,107, Notice of Allowance mailed Feb. 1, 2010", 4 pgs.

"U.S. Appl. No. 11/778,527, Notice of Allowance mailed Jul. 29, 2010", 4 pgs.

"U.S. Appl. No. 11/148,107, Examiner Interview Summary mailed Oct. 9, 2008", 4 pgs.

"U.S. Appl. No. 11/148,107, Notice of Allowance mailed Nov. 23, 2010", 6 pgs.

"U.S. Appl. No. 12/510,962, Non-Final Office Action mailed Dec. 28, 2010", 9 pgs.

"U.S. Appl. No. 10/334,694 Notice of Allowance mailed Oct. 5, 2010", 6 pgs.

"U.S. Appl. No. 10/334,694, Response filed Jul. 27, 2010 to Non-Final Office Action mailed Apr. 30, 2010", 19 pgs.

"U.S. Appl. No. 11/129,050 Notice of Allowance mailed Nov. 1, 2010", 6 pgs.

"U.S. Appl. No. 11/148,107, Notice of Allowance mailed Aug. 30, 2010", 8 pgs.

\* cited by examiner

DETECTION OF MYOCARDIAL ISCHEMIA FROM THE TIME SEQUENCE OF IMPLANTED SENSOR MEASUREMENTS

CROSS-REFERENCE TO RELATED APPLICATIONS

This application is related to the following commonly assigned U.S. patent applications: Ser. No. 10/703,175, entitled "A DUAL USE SENSOR FOR RATE RESPONSIVE PACING AND HEART SOUND MONITORING," filed on Nov. 6, 2003, now issued as U.S. Pat. No. 7,248,923, Ser. No. 10/334,694 entitled "METHOD AND APPARATUS FOR MONITORING OF DIASTOLIC HEMODYNAMICS," filed on Dec. 30, 2002, Ser. No. 10/746,874 entitled "A THIRD HEART SOUND ACTIVITY INDEX FOR HEART FAILURE MONITORING," filed on Dec. 24, 2003, now issued as U.S. Pat. No. 7,115,096, Ser. No. 60/631,742 entitled "CARDIAC ACTIVATION SEQUENCE MONITORING FOR ISCHEMIA DETECTION," filed on Nov. 30, 2004, Ser. No. 11/129,050, entitled "METHOD AND APPARATUS FOR CARDIAC PROTECTION PACING," filed on May 16, 2005, Ser. No. 11/148,107, entitled "ISCHEMIA DETECTION USING HEART SOUND SENSOR," filed on Jun. 8, 2005, U.S. Pat. No. 6,666,826, entitled "METHOD AND APPARATUS FOR MEASURING LEFT VENTRICULAR PRESSURE," filed Jan. 4, 2002, and U.S. patent application Ser. No. 10/795,126, entitled "WIRELESS ECG IN IMPLANTABLE DEVICES," filed on Mar. 5, 2004, now issued as U.S. Pat. No. 7,299,086, each of which is hereby incorporated by reference.

TECHNICAL FIELD

The field generally relates to implantable medical devices and, in particular, but not by way of limitation, to systems and methods for detecting myocardial ischemia.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In addition to electrical events, CFM devices may measure hemodynamic parameters related to chamber filling and contractions. Ischemia occurs when blood flow to cardiac muscles decreases below the metabolic requirements of the heart. Detecting ischemia early is critical to the health of the patient and allows early initiation of treatment. Cardiac muscle cells that are ischemic are electrically irritable and may be more susceptible to abnormal heart rhythms (e.g., fibrillation). Further, ischemia impairs the pumping function of the heart. If left untreated the underlying cause of ischemia which is commonly artherosclerotic disease may lead to myocardial infarction (i.e., heart attack).

SUMMARY

This document discusses, among other things, systems and methods for monitoring cardiac function of a patient or subject. A system example includes a plurality of sensors, a processor, and a response circuit. At least one of the sensors is an implantable sensor. Each sensor produces an electrical sensor signal related to physiologic cardiovascular events of a subject. The processor includes an event sequence detector to permit real-time detection of a time-wise sequential cascade of physiologic cardiovascular events related to myocardial ischemia of the subject and a decision module. The time-wise cascade includes at least first, second, and third physiologic cardiovascular events. The decision module declares whether an ischemic event occurred using at least one rule applied to a temporal relationship of the first, second, and third physiologic cardiovascular events. The response circuit provides a specified response if the ischemic event is declared.

A method example includes sensing first, second, and third implantable sensor signals, each sensor signal including physiologic cardiovascular information, detecting first, second, and third physiologic cardiovascular events from the first, second, and third implantable sensor signals, and declaring whether an ischemic event occurred using at least one rule applied to a temporal relationship of the first, second, and third physiologic cardiovascular events.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
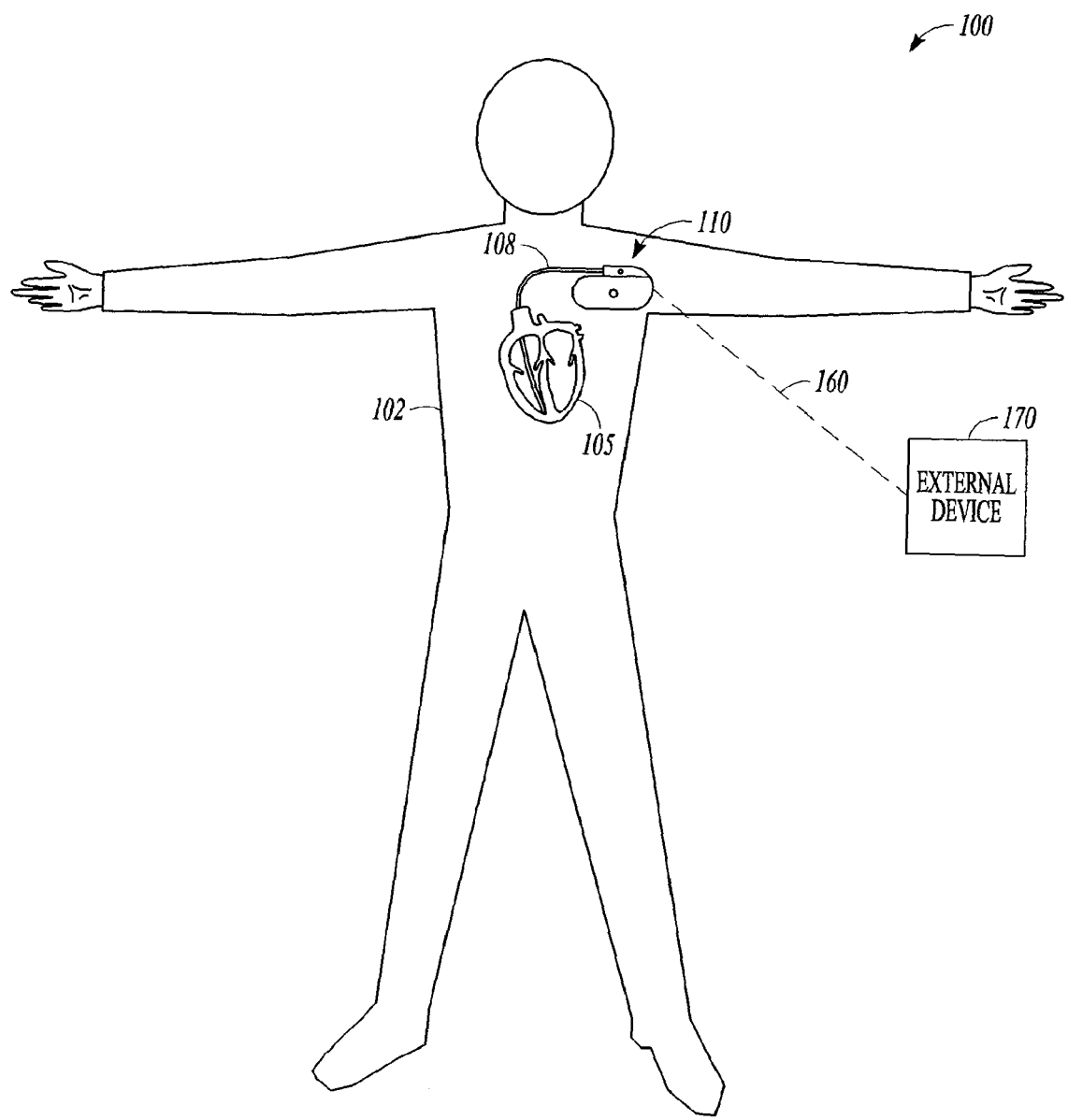
FIG. 1 is a block diagram of portions of a system that uses an implantable medical device (IMD).

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

The functions or algorithms described herein are typically implemented in software or a combination of software and human implemented procedures in one embodiment. The software typically comprises computer executable instructions stored on computer readable media such as memory or other type of storage devices. Further, such functions typically correspond to modules, which are software, hardware, firmware or any combination thereof. Multiple functions are performed in one or more modules as desired, and the embodiments described are merely examples. The software is typically executed on a digital signal processor, ASIC, microprocessor, or other type of processor. The processor may operate as part of an implantable medical device or the processor may operate on a computer system, such as a personal computer, server or other computer system.

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

The IMDs may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Monitoring of electrical signals related to cardiac activity may provide early, if not immediate, diagnosis of ischemia.

Evidence of myocardial ischemia in a subject can become manifest in various ways. Occurrences of coronary blood flow occlusion typically result in an immediate increase in heart rate and a decrease in myocardial shortening, particularly in an ischemic heart-wall segment. Dyssynergy in ventricular contractions also often occurs. Sometimes, abnormalities are detectable after the occlusion in an electrocardiograph (ECG) within thirty seconds to one minute after the occlusion. Myocardial ischemia depresses the peak negative rate of change of pressure (dP/dt) in the left ventricle (LV) and also depresses the LV peak positive dP/dt. Coronary blood flow occlusion may also result in decreased peak endocardial acceleration.

Implantable cardiac rhythm management (CRM) devices are sometimes equipped with implantable sensors that have the capability to detect various physiological variables associated with cardiac and pulmonary function. These sensors are typically used in applications such as rate responsive pacing and advanced patient management. Because myocardial ischemia can result in changes in the various physiological variables, these sensors may also be used for early detection of myocardial ischemia. The difficulty with using such sensors to detect ischemia is that while each sensor may experience a change due to ischemia, the sensor output may not be tailored to be specific to ischemia. Myocardial ischemia results in a series of physiological events that occur in a particular sequence in time beginning with heart-wall abnormalities and ending with S-T segment elevation. Thus, the specificity of ischemia detection can be improved by detecting this time-wise sequence of events using a plurality of sensors that each measure a part of the time sequence of events.

FIG. 1 is a block diagram of portions of a system 100 that uses an implantable medical device (IMD) 110. As one example, the system 100 shown is used to treat a cardiac arrhythmia. The IMD 110 typically includes an electronics unit coupled by a cardiac lead 108, or additional leads, to a heart 105 of a patient 102, or otherwise associated with the heart 105. Examples of IMD 110 include, without limitation, a, pacemaker, a cardioverter, a defibrillator, a cardiac resynchronization therapy (CRT) device, and other cardiac monitoring and therapy delivery devices, including cardiac devices that include or work in coordination with neuro-stimulating devices, drugs, drug delivery systems, or other therapies. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2:
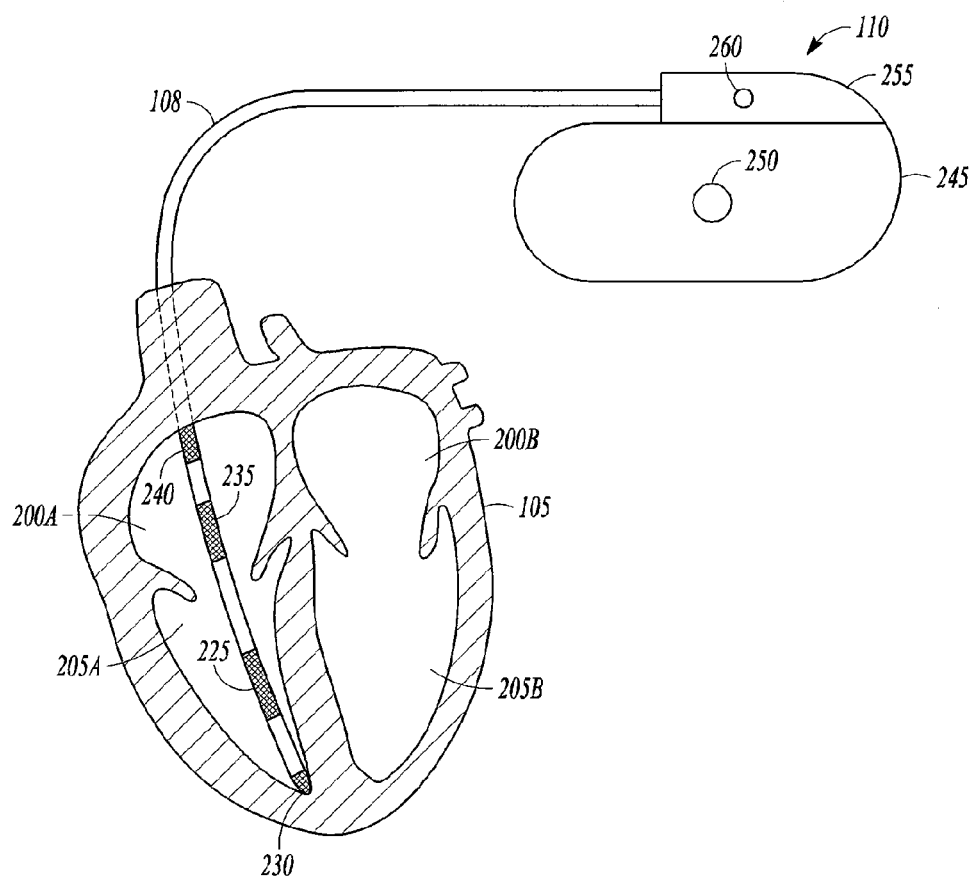
FIG. 2 illustrates an IMD coupled by one or more leads to a heart.

FIG. 2 illustrates an IMD 110 coupled by one or more leads 108 to heart 105. Heart 105 includes a right atrium 200A, a left atrium 200B, a right ventricle 205A, and a left ventricle 205B. Lead 108 includes electrodes (electrical contacts, such as ring electrode 225 and tip electrode 230) disposed in a ventricle 205A of heart 105 for sensing signals, or delivering pacing therapy, or both, to the ventricle 205A. Lead 108 also includes one or more electrodes for placement in the right atrium 200A, such as ring electrode 235 and ring electrode 240, for sensing electrical cardiac signals, delivering pacing therapy, or both sensing signals and delivering pacing therapy. Sensing and pacing allows the IMD 110 to adjust timing of the chamber contractions. For example, IMD 110 can adjust the timing of ventricular contractions with respect to the timing of atrial contractions delay by sensing a contraction in the right atrium 200A and pacing the right ventricle 205A at the desired AV delay time. The IMD also includes can electrode 250 formed on the IMD can 245, and header electrode 260 formed on the IMD header 255.

The IMD 110 optionally also includes additional leads and electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Optionally, lead 108 includes two leads containing two electrodes each. In an example, a first lead includes a tip electrode located in the apex of the right ventricle 205A and a first ring electrode located proximal to the tip electrode. A second lead includes a tip electrode located in the right atrium 200A and a ring electrode located in the right atrium 200A proximal to the tip electrode.

Optionally, IMD 110 includes an additional cardiac lead that includes ring electrodes for placement in a coronary vein extending along a wall of the left ventricle 205B. A lead placed in the left ventricle 205B and a lead placed in the right ventricle 205A may be used to optionally provide resynchronization therapy to the heart 105.

Figure 3A:
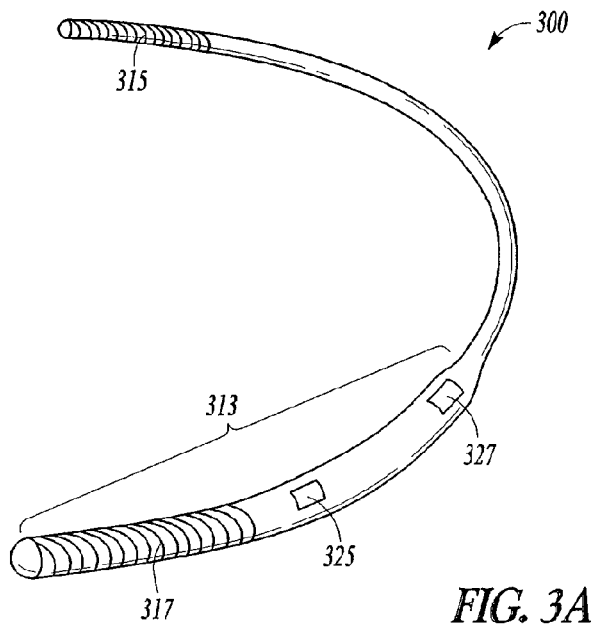
FIGS. 3A-B show an example of an IMD that does not use intravascular leads to sense cardiac signals.
Figure 3B:
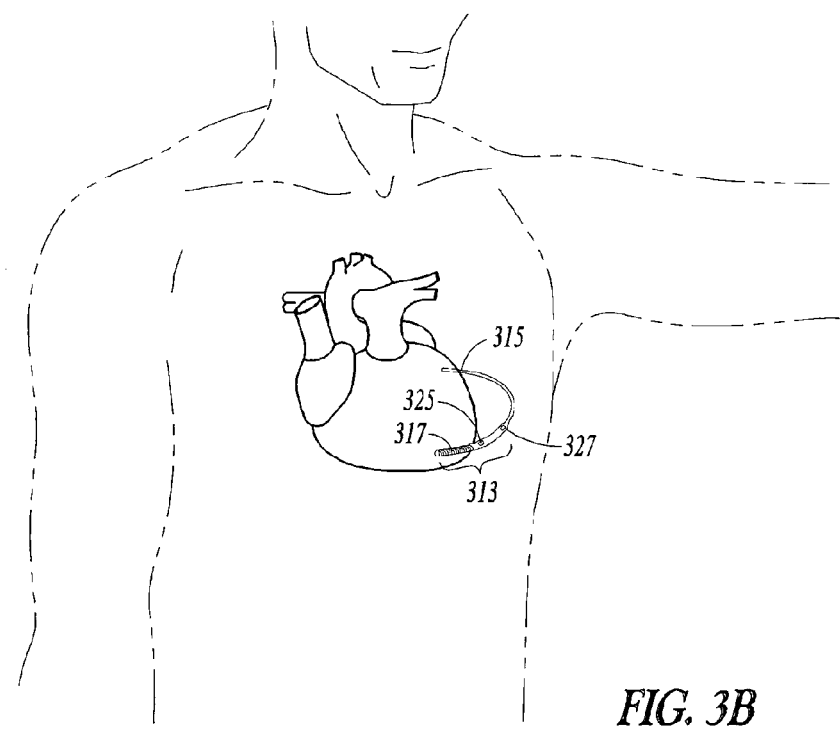

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes. FIGS. 3A-B show an example of an IMD 300 that does not use intravascular leads to sense cardiac signals. FIG. 3A shows that the IMD 300 includes a thicker end 313 to hold the power source and circuits. The IMD 300 also includes electrodes 325 and 327 for remote sensing of cardiac signals. Cardioversion/defibrillation is provided through electrodes 315 and 317. FIG. 3B shows an example of the IMD 300 positioned within a patient.

Myocardial ischemia results in a series of physiological cardiovascular events that occur in a particular sequence in time, which can be referred to as a time-wise cascade of physiological cardiovascular events. Table 1 is a non-exhaustive list of some examples of the physiological cardiovascular events in the time-wise sequential ischemic cascade and includes examples of sensor used to detect the events.

TABLE 1

| Physiologic Event | Magnitude of change | Time to event | Monophasic or Biphasic | Sensor Example |
| --- | --- | --- | --- | --- |
| Regional wall shortening | significant | After a few beats | Monophasic | Cardiac Z or 3D Heart Sound |
| Heart rate increase | ~40% increase | 20-45 sec. | Monophasic | Egram |
| Decrease in chamber relaxation | ~40% decrease | 60 sec. | Biphasic | Cardiac Z or STI |
| Increased chamber filling pressure | Patient dependent change | 30-90 sec. | Monophasic | Heart Sound or Pressure |
| Decrease in chamber contractility | ~20% decrease | 60 sec. | Biphasic | Heart Sound, Cardiac Z, or STI |
| ECG abnormalities | S-T segment elevation | 30 sec. to minutes | Monophasic | |
| Subject pain or discomfort | Patient dependent change | 30 sec. to minutes | N/A | |

The list includes an approximate magnitude of the change when ischemia occurs, the time after ischemia that the event occurs, and whether the change is monophasic or biphasic. Monophasic refers to the indicated change remaining after an ischemic event. Biphasic refers to the change appearing and then disappearing as the heart compensates in response to the ischemic event.

The Table shows that if myocardial ischemia results in regional shortening of a heart wall, it happens fairly quickly. This change can be manifested as left ventricle (LV) wall motion abnormality for example. Myocardial ischemia often results in a reduction in LV contractility which can be detected through measurements of heart sounds and cardiac impedance.

Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. A heart sound sensor produces an electrical signal which is representative of mechanical activity of a patient's heart. Regional shortening causes changes in the heart sounds detectable with a heart sound sensor. A description of systems and methods for sensing wall motion is found in the commonly assigned, co-pending U.S. patent application Ser. No. 11/135,985, entitled "SYSTEMS AND METHODS FOR MULTI-AXIS CARDIAC VIBRATION MEASUREMENTS," filed May 24, 2005, which is incorporated herein by reference.

An accelerometer can be used to provide acceleration signals each indicative of regional cardiac wall motion. One or more accelerometers can be incorporated into a portion of a lead positioned on or in the heart. The accelerometers detect the wall motion abnormality as an abrupt decrease in the amplitude of local cardiac accelerations.

A cardiac impedance sensor senses an electrical impedance signal between electrodes interposed in the heart. For example, in FIG. 2 a cardiac impedance sensor can sense intracardiac impedance of the right ventricle 205A between an electrode placed at the apex of the right ventricle 205A and an electrode placed in the right atrium 200A. A predetermined excitation current is delivered between the electrodes and the impedance is determined from a voltage sensed between the electrodes. A transthoracic impedance of a subject can be measured between the ring electrode 225 and can electrode 250 or header electrode 260.

A cardiac impedance sensor can be used to track an impedance signal along with cardiac contractions and create a baseline impedance or normal impedance signal pattern. Because cardiac impedance is responsive to cardiac contractions, changes due to regional shortening may change the morphology of the impedance swings that occur with each cardiac contraction. In some examples, the impedance signal morphology is compared against the baseline pattern. When the pattern is significantly different, e.g. based on fiducial points in the signal or based on an amplitude distance between the signals (such as a mean absolute deviation or a root-mean-square (RMS) difference), an ischemic event is declared. In some examples, the morphology is compared by assigning a morphology score to the impedance signal. An ischemic event is declared if the morphology score is different from a predetermined threshold score by a specified amount. The morphological changes are typically confirmed by other sensor measurements.

The regional shortening is followed by an increase in the heart rate of a subject. Some subjects may experience about a forty percent increase in rate. Examples of sensors that can detect a heart rate increase include a cardiac signal sensing circuit that includes electrodes as shown in FIG. 2. Some subjects may experience an increase in a ratio of sympathetic cardiac activity to parasympathetic cardiac activity. This can be detected using the sensing electrodes and a measure of variability of ventricular time intervals. In some examples, the change in the sympathetic/parasympathetic ratio can be obtained by sampling of the signal. A morphology template is compared to the stored signals. A morphology score for a normal sinus rhythm is used to the asses the rhythm. Because knowledge of the activity of a subject is useful in obtaining a measure of sympathetic cardiac activity to parasympathetic cardiac activity, such measurements are sometimes made in association with an activity sensor, such as an accelerometer.

The change in heart rate is followed by a decrease in chamber relaxation and by a decrease in chamber contractility. The change in relaxation and contractility is manifested as a change in intra-chamber blood pressure. Rate of pressure change (dP/dt) is an after-load independent measure of left ventricular contraction strength. Some subjects may experience a decrease in heart chamber relaxation as measured by a maximum negative dP/dt of forty percent. Some subjects may experience a decrease in heart chamber contractility as measured by a maximum positive dP/dt of twenty percent.

Examples of sensors that can detect a change in heart chamber contractility or relaxation include a cardiac impedance sensor or electrodes for sensing heart signals. Cardiac impedance changes measure changes in chamber volumes. Regional changes in cardiac relaxation may be measured using measurements of cardiac impedance using an impedance sensor. Similarly, the strength of contraction may be inferred from changes in the rate of decrease of cardiac impedance during cardiac contraction. Peak positive dP/dt may be also inferred from the magnitude of the S1 heart sound.

Changes in heart chamber relaxation and contractility can also be detected using electrodes by measuring the systolic time intervals (STIs). A shortening of an STI may indicate a change in contractility. The availability of intracardiac impedance changes that are sensitive of cardiac volume, electrogram (egram) for cardiac electrical activity, and heart sounds, allows the measurement of systolic time intervals such as the electromechanical systole from the Q wave to the S2 heart sound.

A change in heart chamber contractility can also be measured using a heart sound sensor. Because ischemia is associated with a decrease in ventricular chamber contractility, ischemia is correlated to a decrease in the loudness of the S1 heart sound. A description of systems and methods for monitoring heart sounds is found in U.S. patent application Ser. No. 10/334,694, entitled "METHOD AND APPARATUS FOR MONITORING OF DIASTOLIC HEMODYNAMICS," filed on Dec. 30, 2002, which is incorporated herein by reference.

Near the time of the change in chamber relaxation and in chamber contractility, a subject may experience an increase in filling pressure of the left ventricle. Examples of sensors that can detect an increase in the filling pressure include an implantable cardiac pressure sensor and a heart sound sensor. An implantable cardiac pressure sensor can be used to measure chamber pressure of the left ventricle. In an example, a pressure sensor is implanted in a coronary vessel to determine left ventricle pressure by direct measurement of coronary vessel pressure. A description of systems and methods that use such an implantable pressure sensor is found in Salo et al., U.S. Pat. No. 6,666,826, entitled "METHOD AND APPARATUS FOR MEASURING LEFT VENTRICULAR PRESSURE," filed Jan. 4, 2002, which is incorporated herein by reference. Other cardiac pressure sensors examples include a right ventricle (RV) chamber pressure sensor, a pulmonary artery pressure sensor, and a left atrial chamber pressure sensor.

A heart sound sensor can also be used to detect increased filling pressure. An increase in S3 heart sound activity is known to be an indication of elevated filing pressures. Systems and methods that use an index derived from the S3 heart sound to detect ischemic events are described in commonly assigned, co-pending U.S. patent application Ser. No. 10/746,874, entitled "A THIRD HEART SOUND ACTIVITY INDEX FOR HEART FAILURE MONITORING," filed Dec. 24, 2003, which is incorporated herein by reference.

In some subjects, the increase in filling pressure may be followed by abnormalities in a subject's ECG. An example of such an abnormality is having an S-wave to T-wave ("ST") interval of the ECG that is elevated by a specified amount from an ST interval of a baseline ECG. An example of a sensing circuit that can detect an abnormality is a wireless ECG sensing circuit. A wireless ECG is a signal approximating the surface ECG and is acquired without using surface (skin contact) electrodes. An example of a circuit for sensing the wireless ECG is discussed in commonly assigned, co-pending U.S. patent application Ser. No. 10/795,126, entitled "WIRELESS ECG IN IMPLANTABLE DEVICES," filed on Mar. 5, 2004, which is incorporated herein by reference. An example of a wireless ECG-based ischemia detector is discussed in commonly assigned, co-pending U.S. patent application Ser. No. 11/079,744, entitled "CARDIAC ACTIVATION SEQUENCE MONITORING FOR ISCHEMIA DETECTION," filed on Mar. 14, 2005, which is incorporated herein by reference.

Table 1 includes an entry for subject pain and/or discomfort. This occurs about the same time as the ECG abnormalities and is important information in making a decision about whether the subject is experiencing an ischemic event. It can be seen from the Table that many of the changes in the various physiological variables occur within a minute or so of an ischemic event. The Table thus shows that an IMD can provide early detection of myocardial ischemia.

Figure 4:
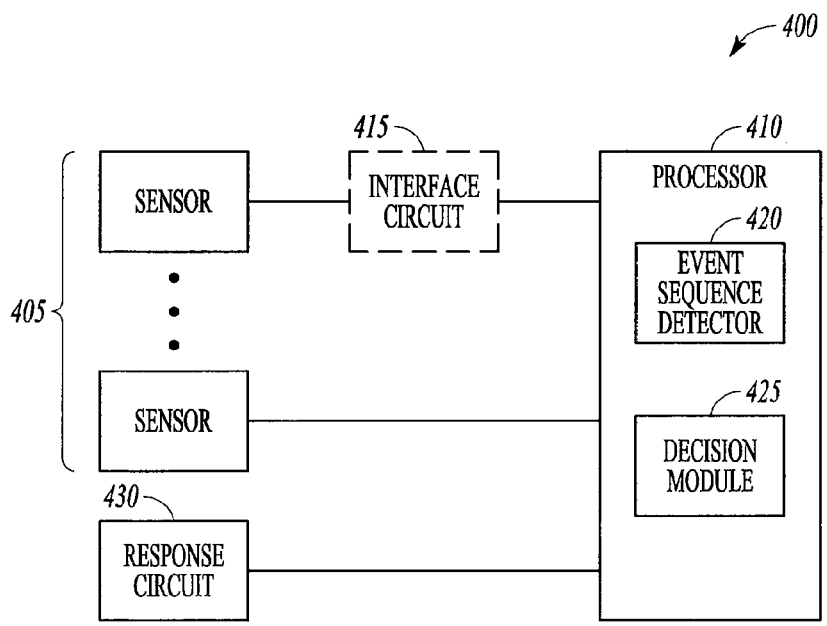
FIG. 4 is a block diagram of portions of an example of a system to detect myocardial ischemia.

FIG. 4 is a block diagram of portions of an embodiment of a system 400 to detect myocardial ischemia. The system 400 includes a plurality of implantable sensors 405. Each of the implantable sensors 405, when implanted in a subject, produces an electrical sensor signal that is related to physiologic cardiovascular events of the subject. The system 400 also includes a processor 410 in electrical communication with the implantable sensors 405. The term electrical communication refers to devices arranged to communicate using electrical signals that influence the operation of the devices. In some examples, the devices are coupled directly. In some examples, the devices communicate electrical signals through intermediate devices, such as devices that include digital or analog circuits. Some of the implantable sensors 405 may include an interface circuit 415 to condition an electrical signal to be compatible for communication with the processor 410.

Examples of the implantable sensors 405 include, without limitation, a heart sound sensor, a three-dimensional (3D) heart sound sensor, a transthoracic impedance measurement circuit, an intracardiac impedance measurement circuit, an electrical cardiac signal sensing circuit, an accelerometer, a blood pressure sensor, and a patient activity sensor.

In some examples, the processor 410 is operable by executing instructions in firmware. In some examples, the processor 410 is operable by executing software instructions. In some examples, the processor 410 is operable through any combination of hardware, software and/or firmware. The processor 410 includes an event sequence detector 420 to permit real-time detection of a time-wise sequential cascade of physiologic cardiovascular events related to myocardial ischemia of a subject. The time-wise cascade includes at least first, second, and third physiologic cardiovascular events. The physiologic cardiovascular events do not have to come from three different sensors. For example, a single heart sound sensor can provide indications of a change in regional wall shortening, an increase in filling pressure, and an increase in heart chamber contractility.

The system 400 also includes a decision module 425 and a response circuit 430. The decision module 425 declares whether an ischemic event occurred using at least one rule applied to a temporal relationship of the first, second, and third physiologic cardiovascular events. For example, the decision module 425 may declare an ischemic event if regional shortening is detected, followed by an increase in heart rate, followed by an ECG abnormality. In another example, subsequent events must fall within a timed duration before the decision module 425 declares an ischemic event. In some examples, the decision module 425 assigns weights to the first, second, and third physiologic cardiovascular events, the weights indicating a likelihood that the corresponding event indicates ischemia.

The response circuit provides a specified response if the ischemic event is declared. Following myocardial infarction (MI), cardiac remodeling begins with expansion of the region of the infarcted tissue and progresses to a chronic expansion in the size and a change in the shape of the entire left ventricle. The consequences include a further impaired hemodynamic performance and a significantly increased risk of developing heart failure, as well as a risk of suffering recurrent MI.

In some examples, the system 400 is included in an implantable medical device (IMD) that includes a therapy circuit, such as a pacing therapy circuit. The response circuit 430 initiates the pacing therapy circuit to provide pacing to protect the heart from ischemic damage caused by the detected ischemic event by delivering a pacing post-conditioning therapy followed by a prophylactic pacing preconditioning therapy. Systems and methods that use post-ischemic event cardiac protection pacing are described in commonly assigned, co-pending U.S. patent application Ser. No. 11/129,050, entitled "METHOD AND APPARATUS FOR CARDIAC PROTECTION PACING," filed on May 16, 2005, which is incorporated herein by reference.

In some examples, the response circuit 430 initiates an indication of the ischemic event. In an example, the response circuit 430 activates an alarm, such as a buzzer or other audible indication to indicate that an ischemic event occurred. In some examples, the system 400 is included in an IMD that includes a communication circuit coupled to the response circuit 430 and the system 400 communicates information about the ischemic event to an external device. The detection of ischemia may trigger a drug delivery device to automatically administer a drug. An indication or alarm provided to the subject has further uses, such as to direct the patient to take a drug, adjust medication, or to seek immediate medical assistance.

Figure 5:
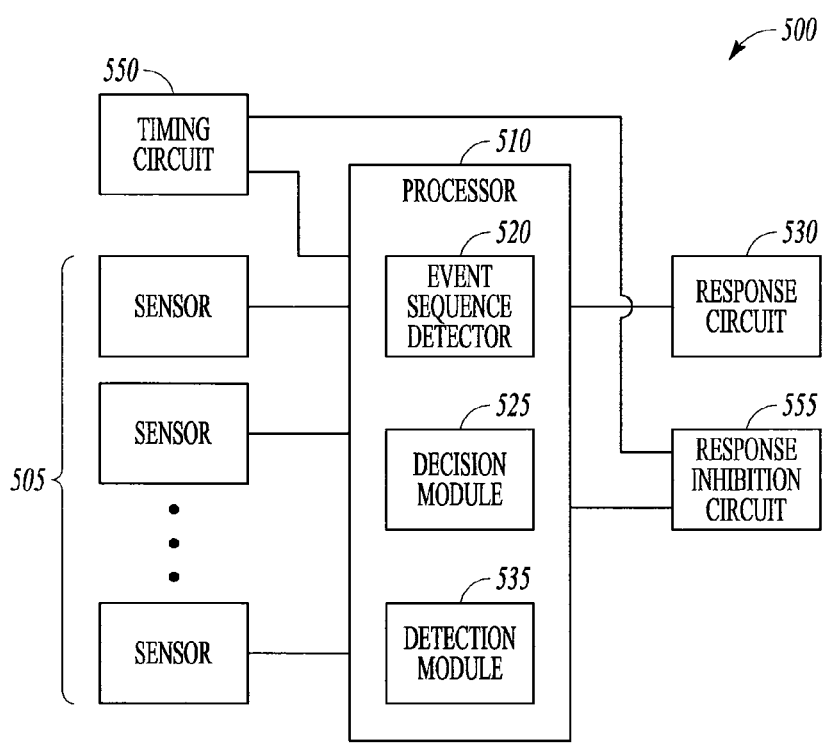
FIG. 5 is a block diagram of portions of an example of another system to detect myocardial ischemia.

FIG. 5 is a block diagram of portions of an embodiment of another system 500 to detect myocardial ischemia. The system 500 includes a plurality of implantable sensors 505, a processor 510, an event sequence detector 520, a decision module 525, a detection module 535, and a response circuit 530. The detection module 535 is in communication with at least one of the implantable sensors 505. In some examples, the detection module 535 is in communication with three or more sensors 505. The implantable sensors 505, when implanted in a subject, produce an electrical sensor signal that is related to physiologic cardiovascular events.

The detection module 535 declares the first physiologic cardiovascular event of the time-wise sequential cascade according to a first detection criterion, or criteria, applied to a first sensor signal, declares the second physiologic cardiovascular event according to a second detection criterion, or criteria, applied to a second sensor signal, and declares the third physiologic cardiovascular event according to a third detection criterion, or criteria, applied to a third sensor signal. Although FIG. 5 shows each of three sensors 505 providing a sensor signal, one of the sensors 505 may provide more than one of the sensor signals. In some examples, more than one sensor signal is used to declare a physiologic cardiovascular event.

In some examples, the system 500 further includes a timing circuit 550 in communication with the detection module 535. The timing circuit 550 initiates a timing window triggered by a detected occurrence of the first physiologic cardiovascular event. The response circuit 530 triggers the specified response upon the second and third physiologic cardiovascular events occurring during the timing window.

Examples of responses include immediately delivering a therapy, communicating an alarm based on the difference between the first sensor signal and the first specified threshold, or both immediately delivering a therapy and communicating an alarm.

In some examples, a detection criterion includes comparing a sensor signal to a predetermined threshold value. In an example, the detection criterion includes detecting that a sensor signal exceeds a predetermined sensor signal amplitude value. In some examples, a detection criterion includes comparing a parameter derived from the sensor signal to predetermined parameter value. In an example, the detection criterion includes a measure of signal variability exceeding a threshold measure. In another example, the detection criterion includes a morphology score for a normal sinus rhythm not meeting a predetermined threshold score value.

In some examples, a detection criterion includes detecting that a sensor signal exceeds a predetermined threshold value for a period of time then not exceeding the predetermined threshold value or being slightly below the value. In some examples, the detection criterion includes hysteresis. For example, a physiologic cardiovascular event is detected when a sensor signal exceeds a first predetermined threshold value for a period of time then not exceeding a second predetermined threshold value. The converse is also possible. A physiologic cardiovascular event is detected when a sensor signal drops below a first predetermined threshold value for a period of time then exceeds a second predetermined threshold value.

In some examples, if at least one of the second and third physiologic events is declared without the first physiologic event being declared, the response circuit 530 initiates a second look at the first physiologic cardiovascular event by changing a detection parameter such as sensitivity. This may occur if the first sensor output is not tailored to be specific to ischemic events. The response circuit 530 modifies the first detection criterion and examines the first sensor signal during a time period before the second physiologic cardiovascular event to determine if the first physiologic cardiovascular event was undetected, and determines the specified response to be delivered.

To examine the first sensor signal, some examples of the system 500 include a sampling circuit to sample the first sensor signal and a memory to store the sampled signal values. In some examples, modifying the detection criterion includes changing a detection threshold for the first sensor signal to determine if the first event was undetected because it was below a threshold (or in some cases above a threshold) of the detection criterion. In some examples, the threshold is applied to the sensor signal itself, such as a signal amplitude threshold. In some examples, the threshold may be applied to a measure derived from the sensor signal, such as a threshold measure of variability of the sensor signal or a morphology score for a normal sinus rhythm not meeting a predetermined threshold value.

If the response circuit 530 determines that the first event was undetected, the response circuit specifies the response of the system 500, such as delivering a therapy or communicating an alarm based on the difference between the first sensor signal and the first specified threshold.

In some examples, the system 500 includes a response inhibition circuit 555. In some examples, the response inhibition circuit 555 is coupled to the detection module 525 and the timing circuit 550. If at least one of the second and third physiologic cardiovascular events is absent during a timing window triggered by the timing circuit, the response inhibition circuit 555 inhibits the specified response.

In some examples, if at least one of the second and third physiologic events is declared without the first physiologic event being declared, the response circuit 530 reduces the detection threshold of one or more of the sensor signals. In some examples, the detection threshold of the sensor signals is set to just above the noise level of the sensor signal. The event sequence detector 520 then determines if the first physiologic event occurs and determines the specified response to be delivered. In some examples, the event sequence detector 520 uses a joint probability distribution of the sensor signals to determine whether an ischemic event occurred.

According to some examples, system 500 can be programmed to customize the criteria used to declare a physiologic cardiovascular event. Suppose that there are 4 events in the cascade that lead to detection of an ischemic event. If only the first two events are used to make an "ischemia detected decision, or declaration, (IDD)" then the detection module 535 may have a given performance measured in terms of 4 parameters: true positives, false positives, false negatives, and time to detection). For example, the time to detection of the event will be smaller if fewer events are used for making the IDD. However the detection will probably exhibit a large number of false positives which may cause nuisance alarms to issue. If more events are used to make an IDD, typically the time to detection will be longer but the specificity will be higher (fewer false positives). While sometimes sensitivity may increase if fewer detectors are used, sensitivity typically decreases with most detection criteria.

Most detection criteria have a trade off between sensitivity (true positives divided by true positives plus false negatives) and false positive rate. The time to detection may also be an issue depending on how quickly the therapy needs to be delivered once ischemia is detected and the therapy side effects. Generally, the higher the sensitivity, the higher is the false positive rate. For a particular patient in whom an ischemic episode may be fatal, a physician may require that the detector be set to high sensitivity (and low time to detection) at the cost of a large false positive rate. Thus, the system 500 can be tailored to a desired response for a particular patient.

Returning to FIG. 4, in some examples, the plurality of implantable sensors 405 and the processor 410 are included in an implantable medical device (IMD). The IMD also includes a communication circuit coupled to the processor 410. The system 400 further includes an external device and the IMD communicates information obtained from the implantable sensors 405 to the external device. In some examples, the external device includes a memory to store data related to physiologic cardiovascular events of the subject and a second processor. The second processor includes a second decision module in communication with the memory. The second decision module declares whether an ischemic event occurred using at least one rule applied to both the temporal relationship of the first, second, and third physiologic cardiovascular events and to the stored data. In some examples, the external device includes an IMD programmer.

In some examples, the external device includes a user interface to receive a user input such as a keyboard, computer mouse, a touch-screen, and the like. The second decision module declares whether an ischemic event occurred using at least one rule applied to a temporal relationship of the first, second, and third physiologic cardiovascular events and the user input. In some examples, the user input includes an indication that the subject is experiencing significant pain or discomfort.

Figure 6:
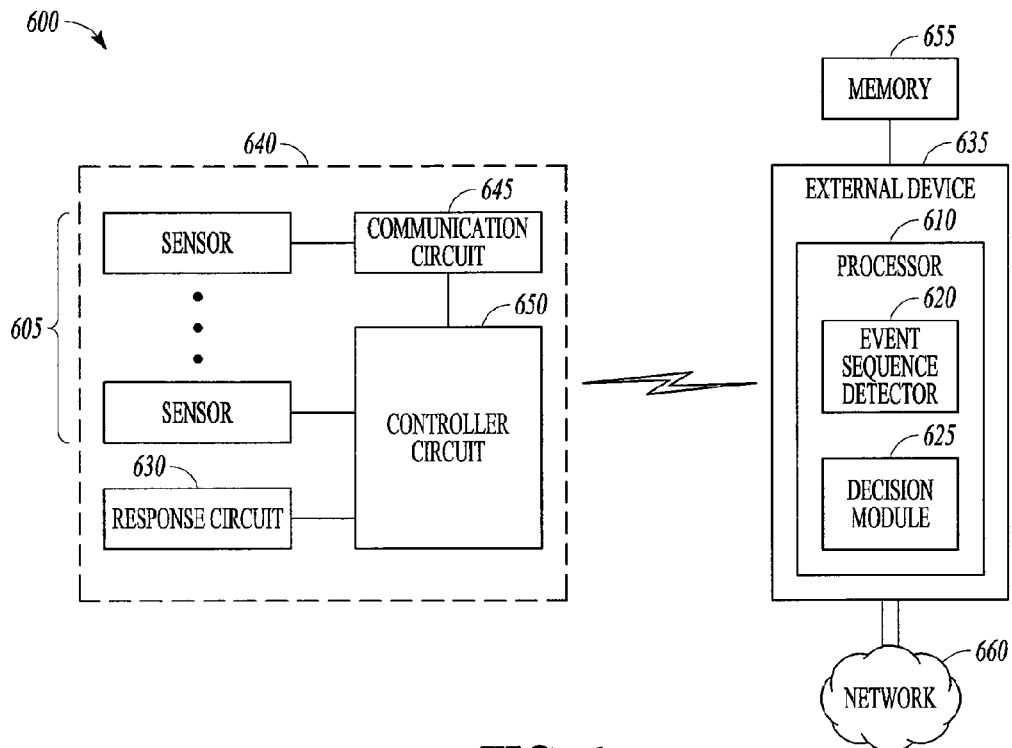
FIG. 6 is a block diagram of portions of an example of another system to detect myocardial ischemia.

In some system examples, the processor 410 and the response circuit 430 are included in an external device and the plurality of implantable sensors 405 are included in an IMD. An example of such a system 600 is shown in FIG. 6. The system 600 includes an external device 635 and an IMD 640. The IMD 640 includes a plurality of implantable sensors 605 and a response circuit 630. In some examples, the external device 635 includes the response circuit 630. In some examples, both the external device 635 and the IMD 640 include a response circuit 630. The IMD 640 also includes a controller circuit 650 and a communications circuit 645. The controller circuit 650 is coupled to the implantable sensors 605 and the response circuit 630. The communication circuit 645 is coupled to the controller circuit 650 and the IMD 640 communicates information obtained from the implantable sensors 605 to the external device 635.

The external device 635 includes a processor 610 having an event sequence detector 620 and a decision module 625. The system 600 further includes a memory 655 in communication with the external device 635 to store data related to physiologic cardiovascular events of the subject. The decision module 625 is configured to declare whether an ischemic event occurred using at least one rule applied to both the temporal relationship of first, second, and third physiologic cardiovascular events and to the stored data. In some examples, the external device 635 includes an IMD programmer. In some examples, the external device 635 includes an input to receive input from the subject. The decision module 625 is configured to declare whether an ischemic event occurred using at least one rule applied to physiologic cardiovascular events that include input that the subject is experiencing significant pain or discomfort. In some examples, the external device 635 includes a server in communication with a network 660. In some examples, the network 660 includes a hospital computer network. In some examples, the network 660 includes the Internet. In some examples, the network 660 is a communications network such as a cell phone network.

In some examples, the system 600 further includes additional sensors that are external to the IMD. In an example, the system 600 includes an external electrocardiograph (ECG) circuit operable to communicate one or more ECG signals to the external device, and wherein the first, second, and third physiologic cardiovascular events include events indicated by the one or more ECG signals.

Figure 7:
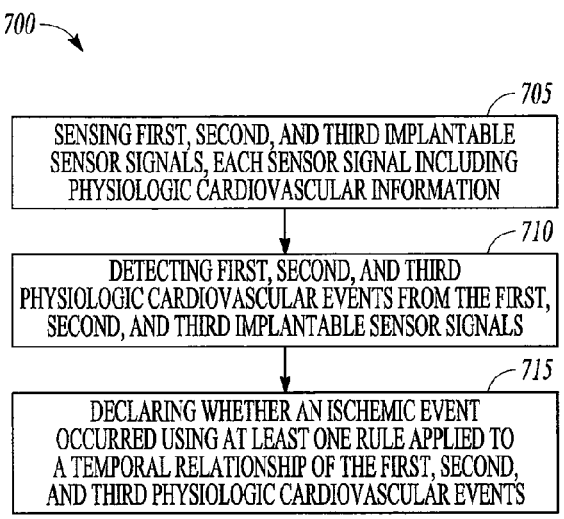
FIG. 7 shows a block diagram of an example of a method for detecting myocardial ischemia.

FIG. 7 shows a block diagram of an example of a method 700 for detecting myocardial ischemia. At 705, first, second, and third implantable sensor signals are sensed. Each sensor signal includes physiologic cardiovascular information. Examples of implantable sensors that provide the implantable sensor signals include, without limitation, a heart sound sensor, a three-dimensional (3D) heart sound sensor, a transthoracic impedance measurement circuit, an intracardiac impedance measurement circuit, an electrical cardiac signal sensing circuit, an accelerometer, a cardiac pressure sensor, and a patient activity sensor. In some examples, sensor signals from external sensors are provided in addition to the signals from the implantable sensors. In some examples, one of the physiologic cardiovascular events is detected using an external electrocardiograph (ECG) signal.

At 710, first, second and third physiologic cardiovascular events are detected from the first, second, and third implantable sensor signals. Examples of physiologic cardiovascular events that are detected from the signals include, without limitation, ventricle wall motion abnormality, an increase in heart rate, a decrease in a heart relaxation interval, an increase in ventricle filling pressure, ventricular chamber dyssynergy, and a decrease in heart contractility. At 715, whether an ischemic event occurred is declared using at least one rule applied to a temporal relationship of the first, second, and third physiologic cardiovascular events. In some examples, one of the physiologic cardiovascular events includes a subject experiencing pain and discomfort. In some examples, the method includes receiving an indication of subject discomfort related to ischemia, and declaring whether an ischemic event occurred at least in part by using the indication.

In some examples of the method 700, detecting the first physiologic cardiovascular event includes detecting a first sensor signal reaching a first specified sensor threshold value. A duration is timed from the detection of the first physiologic cardiovascular event to a scheduled response. In some examples, the scheduled response includes providing a therapy including a delivery of electrical energy, such as pacing for example. In some examples, the scheduled response includes providing an alarm. In some examples, the scheduled response includes providing both therapy and an alarm.

An occurrence of only one physiologic cardiovascular event may indicate that only a low to medium level alarm should be generated. An episode where only one or two out of three or more physiologic cardiovascular events of an ischemic cascade occur may indicate that an ischemic event has not occurred. This depends on the confidence that the events provide in determining that an ischemic event occurred. In some examples, a weight is assigned to one or more of the first, second, and third events according to a likelihood that the event indicates ischemia. In some examples, the scheduled response is inhibited if at least one of the second and third physiologic cardiovascular events is absent during the timing of the duration triggered by the first event.

The scheduled response is altered if at least one of the second and third physiologic cardiovascular events is detected during the timing of the duration. An occurrence of both the first physiologic cardiovascular event and at least one of the second and third physiologic cardiovascular events can be a strong indication that an ischemic event occurred. The alarm is elevated to a high level in this case. In some examples, the scheduled response is altered by immediately providing the therapy or the alarm. In some examples, the scheduled response is altered by providing the response immediately after the timing of the duration.

In some examples, one of the physiologic cardiovascular events may occur but not meet a detection threshold, i.e. a difference is detected between a measurement based on a first sensor signal and a specified first detection criterion applied to the first sensor signal. The method 700 includes continuing to detect physiologic cardiovascular events that occur later in the time-wise sequential ischemic cascade. Whether the second physiologic cardiovascular event occurred is declared using a second detection criterion applied to the second sensor signal, and whether the third physiologic cardiovascular event occurred is declared using a third detection criterion applied to the third sensor signal.

If at least one of the second and third events is declared, the first sensor signal is re-examined during a specified time duration before the declaration of the second or third event. The difference between the measurement based on the first sensor signal and the specified first detection criterion is used to determine a response to the ischemic event. In some examples, the specified response is delivered if the at least one of the second or third events occurred based on the difference between the measurement based on the first sensor signal and the specified first detection criterion, i.e. the first sensor signal indicates that a sub-threshold event occurred. The response includes an alarm, an electrical energy delivery, or both an alarm and the electrical energy delivery.

In some examples, if at least one of the second and third events is declared, then a detection threshold is reduced for at least the first sensor signal. In some examples, detection thresholds for all of the sensors are reduced. The method 700 includes continuing to detect physiologic cardiovascular events. The specified response is delivered if both the first physiologic cardiovascular event and at least one of the second and third physiologic cardiovascular events occur.

Figure 8:
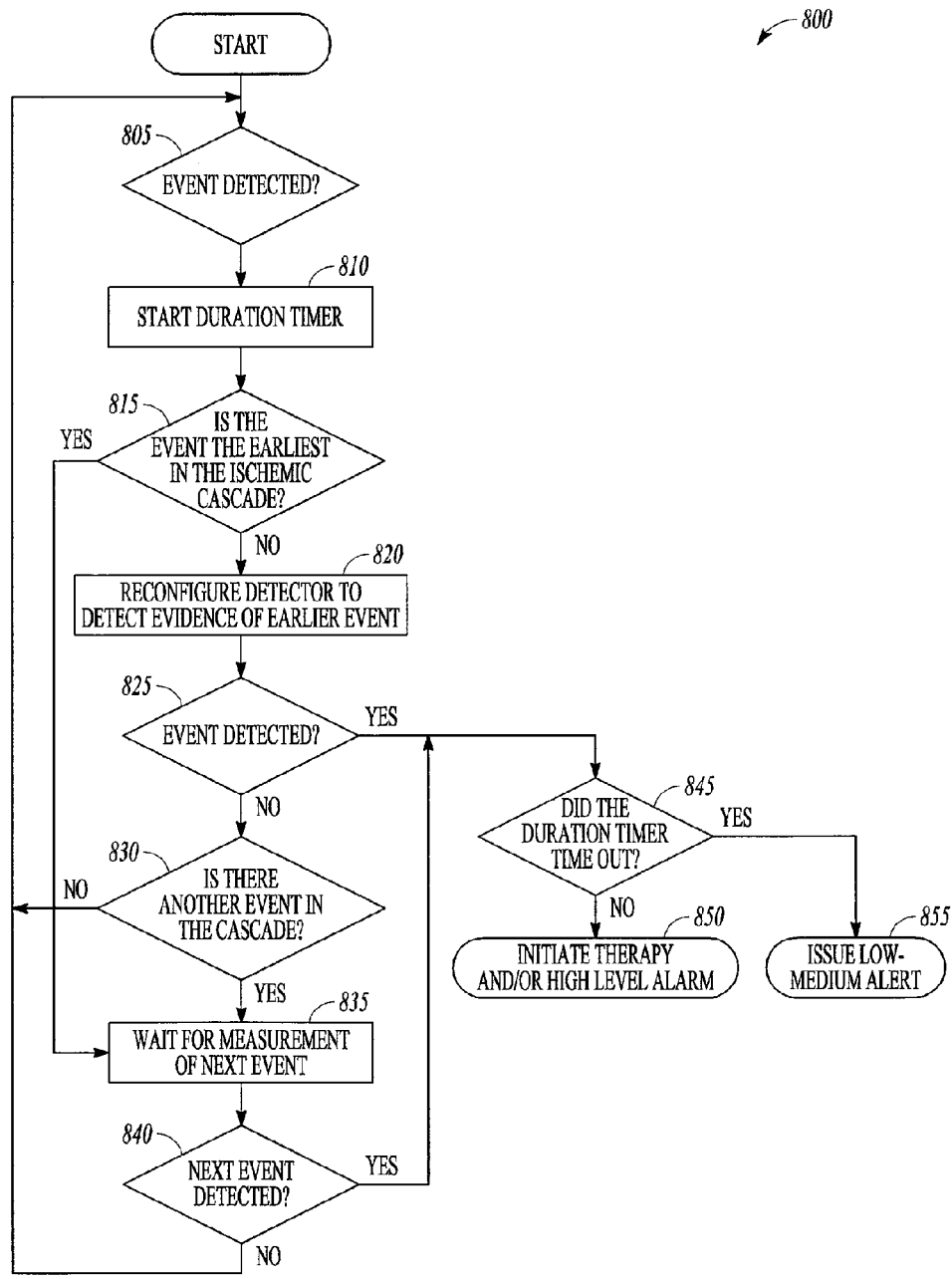
FIG. 8 is a block diagram of an example of another method for detecting myocardial ischemia.

FIG. 8 is a block diagram of another method for detecting myocardial ischemia. At 805 it is determined whether an event in an ischemic cascade occurred. If it did occur, a duration timer is started at 810. At 815, it is determined if the detected event is the earliest in the cascade of events. If the detected event is the earliest event in the cascade, the method 800 waits for the next event to be measured at 835. At 840, if a subsequent event in the cascade is not detected, the method 800 returns to looking for the start of the cascade at 805. If one or more subsequent events in the ischemic cascade do occur, the timer is checked at 845. If the one or more subsequent events occur during the timed duration, at 850 a response is initiated immediately. The response can be electrical therapy or drug therapy, or it can be indicating a high level alarm, or it can be both therapy and an alarm. If one or more subsequent events occur but do not occur during the timed duration, a low to medium level alarm is indicated at 855. Any scheduled therapy response is not altered and is delivered according to the schedule.

Returning to 815, if the first detected event is not the earliest in the ischemic cascade, the event detector is reconfigured to detect evidence of the earlier event at 820. In some examples the signal data from a time period before the first event was detected is then examined. At 825, it is determined if the earlier event is detected by the detection criterion (such as if the event occurred below a detection threshold for example). If there was not an undetected earlier event, at 830 it is determined if there is an upcoming event in the ischemic cascade. If there is not, the method 800 returns to looking for the start of the cascade at 805. If there is an upcoming event, the method 800 waits for the next event to be measured at 835.

If there was an undetected earlier event, the timer is checked at 845. If the one or more subsequent events occur during the timed duration and there was an undetected earlier event, at 850 a response is initiated immediately, otherwise a scheduled response is not altered and is delivered according to the schedule.

Figure 9:
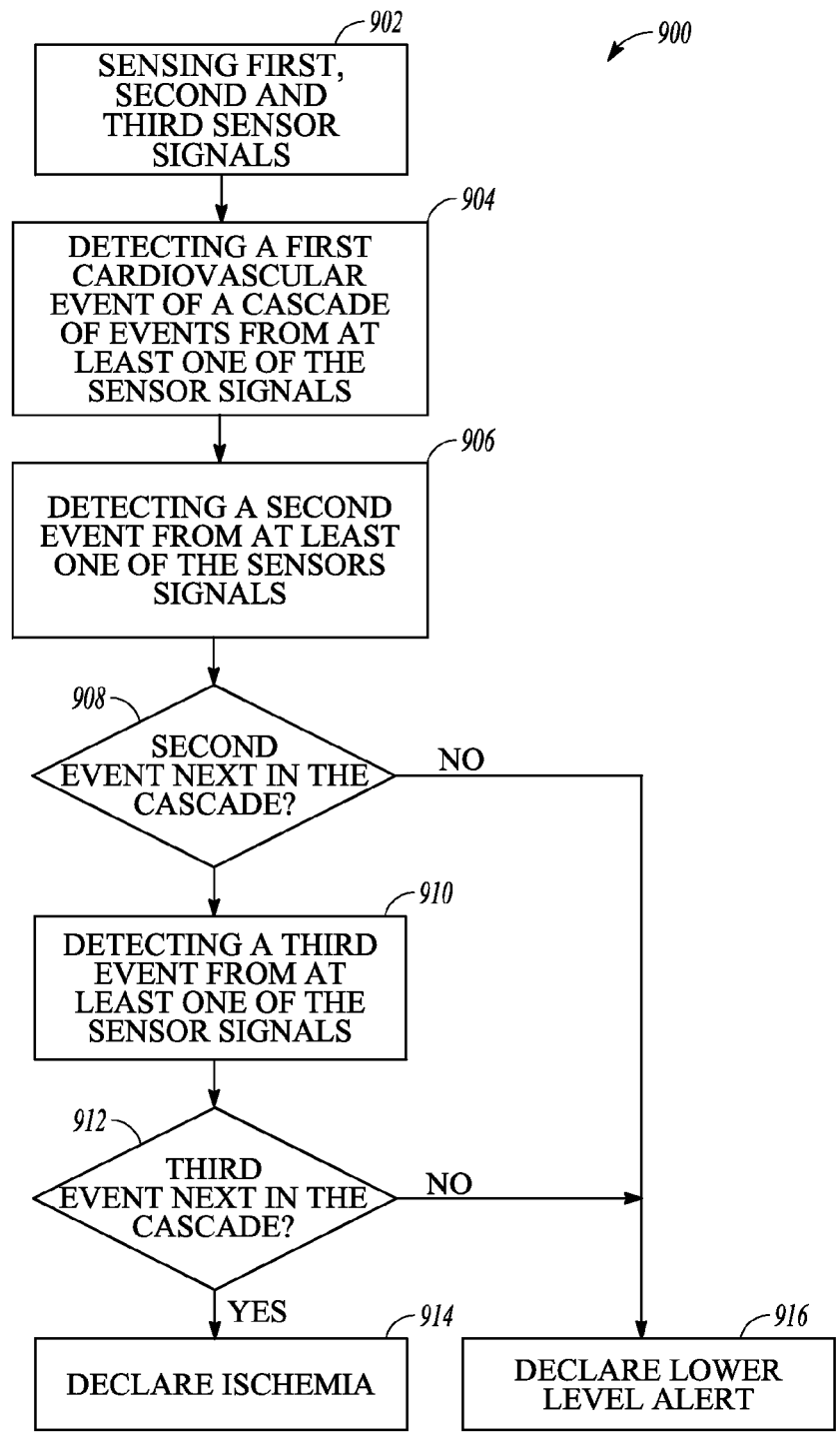
FIG. 9 is flow diagram of yet another example of a method for detecting myocardial ischemia.

FIG. 9 is a block diagram of another method 900 for detecting myocardial ischemia. First, second, and third sensor signals are sensed at 902. A first cardiovascular event and a second event are detected from at least one of the sensor signals at 904 and 906 respectively. If the second event is not next in the cascade at 908, then a lower level alert is declared at 916. If the second event is next in the cascade at 908, then a third event is detected from at least one of the sensor signals at 910. If the third event is not next in the cascade at 912, then a lower level event is declared at 916. If the third event is next in the cascade at 912, then ischemia is declared at 914.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   a plurality of sensors, each sensor operable to produce an electrical sensor signal related to physiologic cardiovascular events of a subject, and wherein at least one of the sensors is capable of being implanted into the subject; and
   a processor in communication with the implantable sensors, wherein the processor comprises:
      an event sequence detector to permit real-time detection of a time-wise sequential cascade of physiologic cardiovascular events related to myocardial ischemia of the subject and a time difference between detected events, wherein the time-wise cascade includes at least first, second, and third physiologic cardiovascular events; and
      a decision module to declare whether an ischemic event occurred using a determined order of occurrence of, and the time difference between occurrence of, the first, second, and third physiologic cardiovascular events; and
      a response circuit, coupled to the decision module, the response circuit operable to provide a specified response if the ischemic event is declared.

2. The system of claim 1, wherein the processor further includes:
   a detection module in communication with at least one of the sensors, wherein the detection module is adapted to:
      declare the first physiologic cardiovascular event according to a first detection criterion applied to a first sensor signal;
      declare the second physiologic cardiovascular event according to a second detection criterion applied to a second sensor signal; and
      declare the third physiologic cardiovascular event according to a third detection criterion applied to a third sensor signal; and
   wherein the response circuit, if at least one of the second and third physiologic events is declared without the first physiologic event being declared, modifies the first detection criterion and examines the first sensor signal during a time period before the second physiologic cardiovascular event to determine if the first physiologic cardiovascular event was undetected, and determines the specified response to be delivered.

3. The system of claim 2, wherein if the response circuit determines that the first event was undetected, the response circuit specifies the response such that the response comprises: (1) immediately delivering a therapy via a therapy circuit, (2) communicating an alarm based on the difference between the first sensor signal and the first specified threshold, or (3) both immediately delivering a therapy and communicating an alarm based on the difference between the first sensor signal and the first specified threshold.

4. The system of claim 1, wherein the processor further includes:
   a detection module in communication with at least one of the sensors, wherein the detection module is adapted to:
      declare the first physiologic cardiovascular event according to a first detection criterion applied to a first sensor signal;
      declare the second physiologic cardiovascular event according to a second detection criterion applied to a second sensor signal; and
      declare the third physiologic cardiovascular event according to a third detection criterion applied to a third sensor signal; and
   a timing circuit, in communication with the detection module, the timing circuit initiating a timing window triggered by the first physiologic cardiovascular event; and
   a response inhibition circuit, coupled to the timing circuit, the decision module, and the response circuit, the response inhibition circuit inhibiting the specified response upon at least one of the second and third physiologic cardiovascular events being absent during the timing window.

5. The system of claim 4, wherein the response circuit provides a response selected from an alarm and a therapy.

6. The system of claim 1, wherein the processor further includes:
   a detection module in communication with at least one of the sensors, wherein the detection module is adapted to:
      declare the first physiologic cardiovascular event according to a first detection criterion applied to a first sensor signal;
      declare the second physiologic cardiovascular event according to a second detection criterion applied to a second sensor signal; and
      declare the third physiologic cardiovascular event according to a third detection criterion applied to a third sensor signal; and
   a timing circuit, in communication with the detection module, the timing circuit initiating a timing window triggered by the first physiologic cardiovascular event; and wherein the response circuit triggers the specified response upon the second and third physiologic cardiovascular events occurring during the timing window.

7. The system of claim 6, comprising means, coupled to the response circuit, for providing an alarm upon detecting the second and third physiologic cardiovascular event.

8. The system of claim 1, wherein one or more of the sensors are selected from the group consisting of:
   a) a heart sound sensor;
   b) a three-dimensional (3D) heart sound sensor;
   c) a transthoracic impedance measurement circuit;
   d) an intracardiac impedance measurement circuit;
   e) an electrical cardiac signal sensing circuit;
   f) a heart rate sensor;
   g) a heart rate variability sensor;
   h) a cardiac pressure sensor; and
   i) a patient activity sensor.

9. The system of claim 1, wherein the first, second, and third physiologic cardiovascular events include events selected from the group consisting of:
   a) left ventricle wall motion abnormality;
   b) an increase in heart rate;
   c) a decrease in heart relaxation interval;
   d) increased ventricle filling pressure; and
   e) a decrease in heart contractility.

10. The system of claim 1, wherein the processor and the response circuit are included in an external device and the plurality of implantable sensors are included in an implantable medical device (IMD), and wherein the IMD further includes:
   a controller circuit, coupled to the implantable sensors and the response circuit; and
   a communication circuit, coupled to the controller circuit, wherein the IMD is operable to communicate information obtained from the sensors to the external device; and
   wherein the system further comprises a memory in communication with the external device, the memory to store data related to physiologic cardiovascular events of the subject, and wherein the decision module is configured to declare whether an ischemic event occurred using at least one rule applied to both the temporal relationship of the first, second, and third physiologic cardiovascular events and to the stored data.

11. The system of claim 10, wherein the external device includes a remote server in communication with the IMD over a communications or computer network.

12. The system of claim 10, wherein the external device includes an IMD programmer.

13. The system of claim 1, wherein the plurality of implantable sensors and the processor are included in an implantable medical device (IMD), wherein the IMD further includes a communication circuit coupled to the processor, and wherein the system further comprises an external device, wherein the IMD is operable to communicate information obtained from the implantable sensors to the external device.

14. The system of claim 13, wherein the external device includes:
   a memory to store data related to physiologic cardiovascular events of the subject; and
   a second processor including a second decision module in communication with the memory, wherein the second decision module is configured to declare whether an ischemic event occurred using at least one rule applied to both the temporal relationship of the first, second, and third physiologic cardiovascular events and to the stored data.

15. The system of claim 13, wherein the external device includes an IMD programmer.

16. The system of claim 15, wherein the external device includes a user interface to receive a user input and the decision module is operable to declare whether an ischemic event occurred using at least one rule applied to a temporal relationship of the first, second, and third physiologic cardiovascular events and the user input.

17. The system of claim 10, wherein the system further includes an external electrocardiograph (ECG) circuit operable to communicate one or more ECG signals to the external device, and wherein the first, second, and third physiologic cardiovascular events include events indicated by the one or more ECG signals.

18. The system of claim 1, wherein the decision module comprises weights assigned to the first, second, and third physiologic cardiovascular events, the weights indicating a likelihood that the corresponding event indicates ischemia.

19. The system of claim 1, wherein the processor further includes:
   a detection module in communication with at least one of the sensors, wherein the detection module is adapted to:
      declare the first physiologic cardiovascular event according to a first detection criterion applied to a first sensor signal;
      declare the second physiologic cardiovascular event according to a second detection criterion applied to a second sensor signal; and
      declare the third physiologic cardiovascular event according to a third detection criterion applied to a third sensor signal; and
   wherein the response circuit, if at least one of the second and third physiologic events is declared without the first physiologic event being declared, reduces a detection threshold of one or more of the sensor signals and determines the specified response to be delivered if the ischemic event is subsequently declared.

20. A method of operating a device comprising:
   sensing at least first, second and third sensor signals using the device, each sensor signal including physiologic cardiovascular information and at least one sensor signal provided by an implantable sensor;
   detecting, using the device, a time-wise sequential cascade of at least first, second, and third physiologic cardiovascular events from the first, second, and third implantable sensor signals and a time difference between detected events;
   declaring, using the device, whether an ischemic event occurred from a determined order of occurrence of, and the time difference between occurrence of, the first, second, and third physiologic cardiovascular events; and
   providing a specified device response if the ischemic event is declared.

21. The method of claim 20, wherein detecting the first physiologic cardiovascular event includes detecting a first sensor signal reaching a first specified sensor threshold value, and wherein the method further includes:
   timing a duration from the detection of the first physiologic cardiovascular event to a scheduled response; and
   altering the scheduled response if at least one of the second and third physiologic cardiovascular events is detected during the timing of the duration.

22. The method of claim 21, wherein altering the scheduled response includes immediately delivering the response upon detecting at least one of the second and third physiologic cardiovascular events, wherein the response includes at least one of an alarm and a delivery of an electrical energy.

23. The method of claim 21, comprising delivering an altered response after timing the duration.

24. The method of claim 21, including inhibiting the scheduled response if at least one of the second and third physiologic cardiovascular events is absent during the timing of the duration.

25. The method of claim 20, comprising:
- detecting a difference between a measurement based on a first sensor signal and a specified first detection criterion applied to the first sensor signal;
- declaring whether the second physiologic cardiovascular event occurred using a second detection criterion applied to the second sensor signal;
- declaring whether the third physiologic cardiovascular event occurred using a third detection criterion applied to the third sensor signal; and
- if at least one of the second and third events is declared, then using the difference between the measurement based on the first sensor signal and the specified first detection criterion, during a specified time duration before the declaration of the second or third event, to determine a response to the ischemic event.

26. The method of claim 25, comprising delivering the response, based on the difference between the measurement based on the first sensor signal and the specified first detection criterion, in response to the declared second or third event, wherein the delivered response includes at least one of an alarm and an electrical energy delivery.

27. The method of claim 20, including assigning a weight to one or more of the first, second, and third events according to a likelihood that the one of the first, second, and third events indicates ischemia.

28. The method of claim 20, including receiving an indication of subject discomfort related to ischemia, and declaring whether an ischemic event occurred at least in part by using the indication.

29. The method of claim 20, including detecting at least one of the first, second, and third physiologic cardiovascular events from an external electrocardiograph (ECG) signal.

30. The method of claim 20, comprising:
- detecting a difference between a measurement based on a first sensor signal and a specified first detection criterion applied to the first sensor signal;
- declaring whether the second physiologic cardiovascular event occurred using a second detection criterion applied to the second sensor signal;
- declaring whether the third physiologic cardiovascular event occurred using a third detection criterion applied to the third sensor signal; and
- if at least one of the second and third events is declared, then reducing a detection threshold for at least the first sensor signal.

* * * * *